(12) United States Patent
Drew

(10) Patent No.: US 10,719,584 B2
(45) Date of Patent: Jul. 21, 2020

(54) MEDICAL FLUID DELIVERY DEVICE PROGRAMMING

(75) Inventor: Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 439 days.

(21) Appl. No.: 13/358,140

(22) Filed: Jan. 25, 2012

(65) Prior Publication Data

US 2012/0209241 A1 Aug. 16, 2012

Related U.S. Application Data

(60) Provisional application No. 61/441,460, filed on Feb. 10, 2011.

(51) Int. Cl.
*G06F 19/00* (2018.01)
*A61M 5/142* (2006.01)
*A61M 5/168* (2006.01)

(52) U.S. Cl.
CPC ..... *G06F 19/3468* (2013.01); *A61M 5/14276* (2013.01); *A61M 5/16831* (2013.01); *A61M 2005/14208* (2013.01); *A61M 2202/0464* (2013.01)

(58) Field of Classification Search
CPC .............. A61M 2205/50; A61M 5/142; A61M 2005/14208; A61M 5/14276; A61M 5/14244
USPC ...... 604/890.1, 891.1, 502, 506–508, 65–67, 604/151–155
See application file for complete search history.

(56) References Cited

U.S. PATENT DOCUMENTS

| 4,619,653 A | 10/1986 | Fischell |
| 4,731,051 A | 3/1988 | Fischell |
| 5,009,641 A * | 4/1991 | Gorton ................. A61M 5/142 128/DIG. 12 |
| 5,088,981 A * | 2/1992 | Howson et al. ................ 604/31 |
| 5,609,575 A * | 3/1997 | Larson .............. A61M 5/14224 604/65 |

(Continued)

FOREIGN PATENT DOCUMENTS

| EP | 0372863 A2 | 6/1990 |
| GB | 2174218 A | 10/1986 |

(Continued)

OTHER PUBLICATIONS

International Search Report and Written Opinion from PCT/US2012/002692, dated Aug. 8, 2012.

*Primary Examiner* — Rebecca E Eisenberg
*Assistant Examiner* — Weng Lee
(74) *Attorney, Agent, or Firm* — Shumaker & Sieffert, P.A.

(57) ABSTRACT

In some aspects, systems, devices, and techniques for programming a medical fluid delivery device are described. In one example, the disclosure relates to a system including a medical fluid delivery device configured to deliver a therapeutic agent to a patient, and a processor. The processor may be configured to receive a proposed therapy dosing program that defines a fluid therapy for delivery to a patient via a medical fluid delivery device for a first period of time, determine a total dosage over a second period of time, where the second period of time at least partially overlaps the first period of time, and compare the total dosage over the second period of time to a reference dosage.

36 Claims, 11 Drawing Sheets

(56) References Cited

U.S. PATENT DOCUMENTS

| | | | |
|---|---|---|---|
| 6,796,956 B2* | 9/2004 | Hartlaub et al. | 604/65 |
| 7,967,806 B2* | 6/2011 | Jasperson | A61M 5/14276 |
| | | | 604/502 |
| 2005/0177096 A1 | 8/2005 | Bollish et al. | |
| 2005/0277911 A1* | 12/2005 | Stewart et al. | 604/890.1 |
| 2009/0043290 A1 | 2/2009 | Villegas et al. | |
| 2009/0209938 A1* | 8/2009 | Aalto-Setala | 604/503 |

FOREIGN PATENT DOCUMENTS

| | | |
|---|---|---|
| WO | 2003/053498 A2 | 7/2003 |
| WO | 2004/037323 A1 | 5/2004 |
| WO | 2010/025795 A1 | 3/2010 |

\* cited by examiner

MEDICAL FLUID DELIVERY DEVICE PROGRAMMING

This application claims the benefit of U.S. Provisional Application Ser. No. 61/441,460, to Drew, filed Feb. 10, 2011, and entitled "MEDICAL FLUID DELIVERY DEVICE PROGRAMMING," which is incorporated herein by reference in its entirety.

TECHNICAL FIELD

This disclosure relates to programming of medical devices and, in particular, programming of medical fluid delivery devices.

BACKGROUND

A variety of medical devices are used for chronic, i.e., long-term, delivery of therapy to patients suffering from a variety of conditions, such as chronic pain, tremor, Parkinson's disease, epilepsy, urinary or fecal incontinence, sexual dysfunction, obesity, spasticity, or gastroparesis. Pumps or other medical fluid delivery devices may be used for chronic delivery of therapeutic agents, such as drugs. Typically, such fluid delivery devices provide therapy continuously or periodically according to parameters contained within a program. A program may comprise respective values for each of a plurality of parameters, specified by a clinician. The fluid delivery devices may be implantable medical devices that receive the program from a programmer controlled by the clinician.

Implantable fluid delivery devices are intended to provide a patient with a therapeutic output to alleviate or assist with a variety of conditions. Typically, such devices provide a therapeutic output under specified conditions on a recurring basis. One type of implantable fluid delivery device is a drug infusion device which can deliver a fluid medication to a patient at a selected site. A drug infusion device may be implanted at a location in the body of a patient and deliver a fluid medication through one or more catheters to a selected delivery site in the body. Drug infusion devices, such as implantable drug pumps, include fluid reservoirs that may be self-sealing and may be accessible through ports. A drug infusion device may be configured to deliver a therapeutic agent from the fluid reservoir to a patient according to a therapy program, which may, for example, specify a rate of delivery by the IMD of a fluid delivered to the patient.

SUMMARY

In general, the disclosure relates to techniques for programming therapy delivered to a patient via a medical fluid delivery device. The therapy delivered to the patient may be delivered by the medical fluid delivery device according to one or more therapy dosing programs defined by a clinician or other authorized user. Prior to being used to define therapy actually delivered to a patient via the medical fluid delivery device, one or more processors, e.g., a processor of an external programming device, may evaluate a proposed therapy dosing program that defines the delivery of therapy to a patient over a first overall duration of time. In particular, the processor may compare the total dosage of a medical fluid proposed for delivery to a patient during a window of time (or "analysis window") that includes a portion of the larger, first overall duration of time of the therapy program to a reference dosage. In some examples, the reference dosage used for the comparison may be defined to correspond to the duration of the analysis window, e.g., a dosage range that may the suitable for delivery to the patient based on the duration of the analysis window.

In one example, the disclosure relates to a method comprising receiving a proposed therapy dosing program that defines a fluid therapy for delivery to a patient via a medical fluid delivery device for a first period of time; determining a total dosage over a second period of time, wherein the second period of time at least partially overlaps the first period of time; and comparing the total dosage over the second period of time to a reference dosage.

In another example, the disclosure relates to a system comprising a medical fluid delivery device configured to deliver a therapeutic agent to a patient, and a processor configured to receive a proposed therapy dosing program that defines a fluid therapy for delivery to a patient via a medical fluid delivery device for a first period of time, determine a total dosage over a second period of time, wherein the second period of time at least partially overlaps the first period of time, and compare the total dosage over the second period of time to a reference dosage defined for the second period of time.

In another example, the disclosure relates to a system comprising means for receiving a proposed therapy dosing program that defines a fluid therapy for delivery to a patient via a medical fluid delivery device for a first period of time, means for determining a total dosage over a second period of time, wherein the second period of time at least partially overlaps the first period of time, and means for comparing the total dosage over the second period of time to a reference dosage.

In another example, the disclosure relates to a non-transitory computer-readable storage medium comprising instructions that cause one or more processors to receive a proposed therapy dosing program that defines a fluid therapy for delivery to a patient via a medical fluid delivery device for a first period of time, determine a total dosage over a second period of time, wherein the second period of time at least partially overlaps the first period of time, and compare the total dosage over the second period of time to a reference dosage.

The details of one or more examples are set forth in the accompanying drawings and the description below. Other features, objects, and advantages will be apparent from the description and drawings, and from the claims.

DETAILED DESCRIPTION

Figure 1:
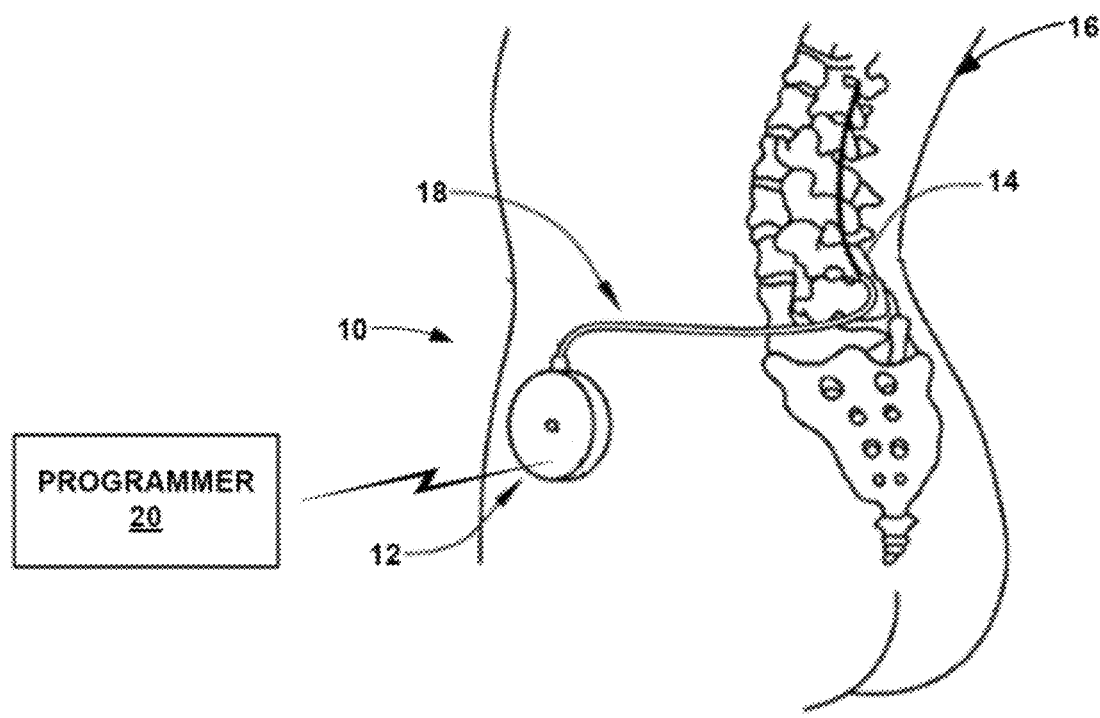
FIG. 1 is a conceptual diagram illustrating an example of a fluid delivery system including an implantable medical device configured to deliver a therapeutic agent to a patient via a catheter.

In general, the disclosure relates to techniques for programming therapy delivered to a patient via a medical fluid delivery device. The therapy delivered to the patient may be delivered by the medical fluid delivery device according to one or more therapy dosing programs defined by a clinician or other authorized user. Prior to being used to define therapy actually delivered to a patient via the medical fluid delivery device, one or more processors, e.g., a processor of an external programming device, may evaluate a proposed therapy dosing program that defines the delivery of therapy to a patient over a first overall period of time. In particular, the processor may compare the total dosage of a medical fluid proposed for delivery to a patient during a window of time (or "analysis window") that overlaps at least a portion of the first overall period of time of the therapy program to a reference dosage. In some examples, the reference dosage used for the comparison may be defined based on the duration of the analysis window. In some examples, the analysis window may be "swept" across all or portions of the overall period of time, in a substantially continuous or incremental manner, to evaluate the therapy defined by the proposed therapy program. In some examples, an indicator indicative of the comparison may be presented to a user via a user interface of, e.g., a programming device. In some examples, the processor may determine whether to apply the therapy dosage program to define therapy actually delivered to the patient via the medical fluid delivery device.

Medical fluid delivery devices are useful for treating, managing or otherwise controlling various patient conditions or disorders, such as, but not limited to, pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical fluid delivery devices may be configured to deliver one or more therapeutic agents, alone or in combination with other therapies, such as electrical stimulation, to one or more target sites within a patient. For example, in some cases, a medical fluid delivery device may deliver insulin to a patient with diabetes. The medical fluid delivery device may be implanted in the patient for chronic therapy delivery (e.g., longer than a temporary, trial basis) or temporary delivery.

For example, in some cases, a medical fluid delivery device may deliver pain-relieving drug(s) to patients with chronic pain, insulin to a patient with diabetes, or other fluids to patients with different disorders. The device may be implanted in the patient for chronic therapy delivery or temporary delivery. For ease of description, examples of the disclosure are primarily described with regard to an implantable fluid delivery device for chronic therapy delivery. However, examples of the disclosure may also be applicable to external fluid delivery devices or fluid delivery device that are only partially implanted in a patient, e.g., devices including one or more percutaneously implanted catheters, for chronic or temporary therapy delivery.

An implantable fluid delivery device may deliver one or more therapeutic fluids to a patient according to one or more therapy dosing programs (also referred to herein as "dosing programs"). As used in this disclosure, the term therapy dosing program generally refers to a program sent to an implantable fluid delivery device by a device for programming the implantable fluid delivery device (or preprogrammed on the implantable fluid delivery device prior to implant) that causes the implantable fluid delivery device to deliver fluid at a certain rate at a certain time. The dosing program may include, for example, definitions of a priming bolus, a bridging bolus, a supplemental bolus, and a therapy schedule. A therapy dosing program may include additional information, such as patient information, permissions for a user to add a supplemental bolus, historical therapy schedules, fluid or drug information, or other information.

A therapy schedule generally defines the rate (which may be zero) at which to administer fluid, or a drug or drug combination within the fluid, at a specific time to a patient. In particular, the therapy schedule may define one or more programmed doses, which may be periodic or aperiodic, each dose including a rate and a duration of time over which to deliver the desired dose. Rate generally refers to the amount of drug delivered over a period of time, and may change over the course of a therapy schedule such that a drug may be delivered at different rates at different times. Although delivery of drugs may be described for purposes of illustration, the techniques described in this disclosure may be useful in delivery of various therapeutic fluids. Accordingly, description of the delivery of drugs should not be considered limiting with respect the techniques broadly described in this disclosure.

Figure 5:
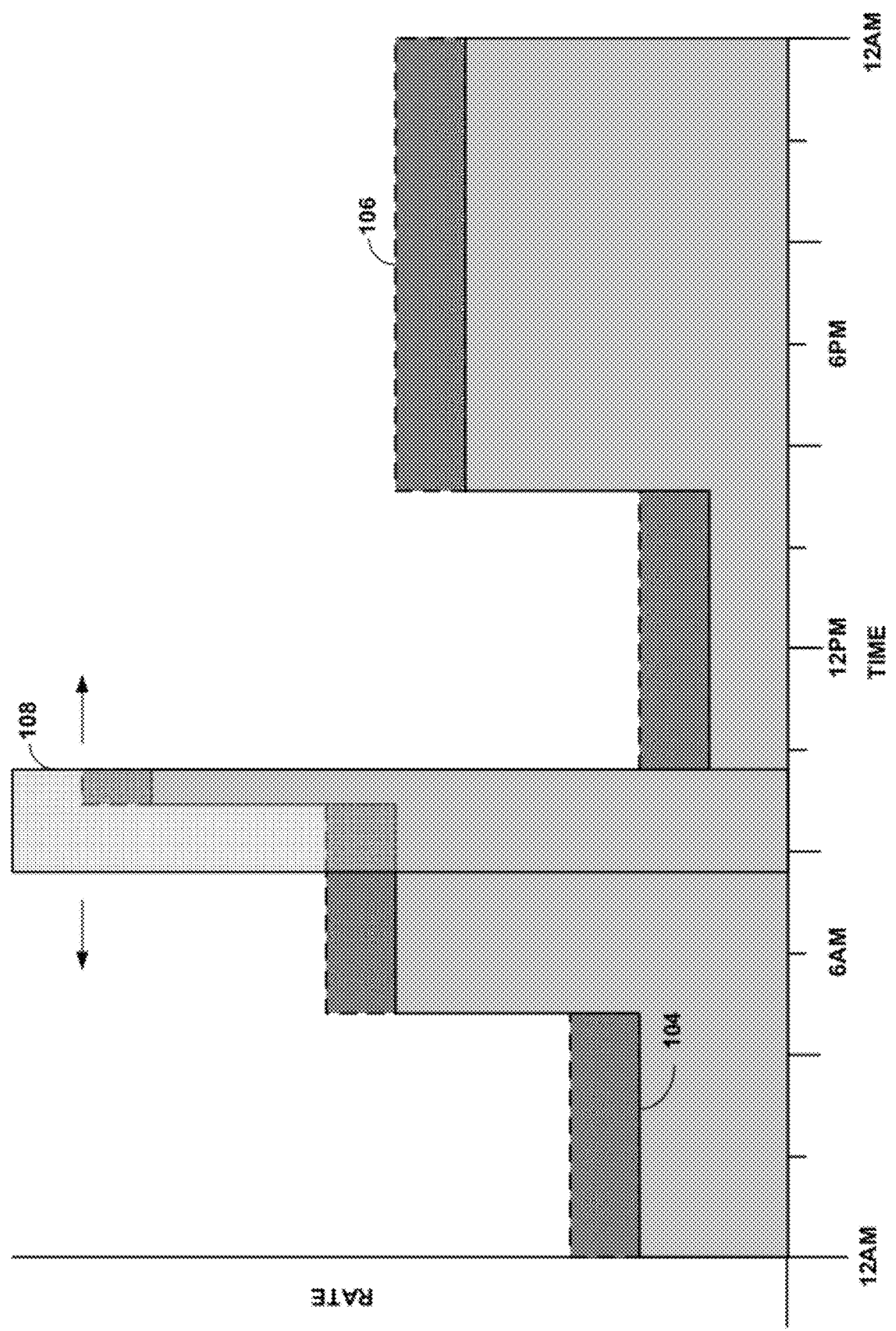
FIG. 5 is a conceptual diagram illustrating an example representation of an example therapy defined by an example therapy dosing program.

A therapy schedule may include one or more fluid delivery profiles for determining the rate of drug delivery at a given time. A fluid delivery profile may be graphically represented by plotting the rate of fluid delivery versus time defined by a therapy schedule for a given period of time, e.g., hour, day, or week. An example of a fluid delivery profile is illustrated in FIG. 5, which is described further below. In some examples, to maintain therapeutic efficacy therapy, the rate at which fluid is delivered to a patient can vary temporally, e.g., rather than maintaining a constant rate of fluid delivery over a given time period. Accordingly, a clinician may define one or more therapy schedules for a patient that causes the rate of a fluid delivery being delivery to the patient to change on a temporal basis. Changes to the rate at which fluid is delivered to a patient from the implantable medical device may correspond to "steps" or "ramps" of a fluid delivery profile.

A priming bolus refers to a bolus delivered by the implantable fluid delivery device to move the fluid to the distal tip of the catheter, i.e., the tip of the catheter that is remote from the reservoir and internal tubing, if applicable. Once the fluid is primed to the distal tip of the catheter, the IMD is ready to deliver fluid to the patient from the distal tip, e.g., via one or more fluid outlets at or near the distal tip. The device delivers the priming bolus during a "priming phase" to prepare the device for delivery of fluid to the patient.

An implantable fluid delivery device also may perform a "bridging" bolus when a new fluid is inserted into a reservoir of the device while an old fluid is still present in the device, e.g., within internal tubing of the device and/or within a catheter connected to the device. The bridging bolus is performed to define a rate at which to deliver the old fluid until the old fluid is completely delivered out of the catheter and to the patient such that the device contains only the new fluid. In some instances, this action by the implantable fluid delivery device may be referred to as a bridging bolus.

A supplemental bolus is a bolus administered to the patient outside of the therapy schedule. The terms independent bolus, one-time bolus, and therapeutic bolus may also be used in this disclosure to refer to a supplemental bolus. In particular, therapeutic bolus and supplemental bolus may be used generally interchangeably in this disclosure. In one example, the implantable fluid delivery device may administer a supplemental bolus before the implantable fluid delivery device begins administering doses of fluid according to the therapy schedule. In another example, the implantable fluid delivery device may administer a supplemental bolus during the therapy schedule, e.g., to override or supplement the therapy schedule in response to clinician instruction or patient request. A supplemental bolus delivered based on a patient request may be referred to in some instances as a patient bolus. The therapy dosing program may define periods during which the delivery of a requested supplemental therapy bolus is authorized or, conversely, not authorized.

A clinician or other authorized user may create the one or more therapy dosing programs that a fluid delivery device will use to deliver therapy to a patient during an initial programming session. In the case of an implantable fluid delivery device, the initial programming session may occur shortly after the device is implanted in the patient. The therapy dosing created during the initial programming session may be applied by a processor of the implantable fluid delivery device to define therapy actually delivered to the patient during and after the initial programming session. Subsequently, a clinician or other user may modify one or more of the therapy dosing programs defined during the initial programming session and/or create one or more new therapy dosing programs during one or more follow-up programming sessions.

In either case, the one or more therapy dosing programs created during a programming session may be used by a processor of an implantable fluid delivery device to control therapy delivered to the patient over a predefined period of time. For example, a therapy dosing program may be created that includes a therapy schedule defining the delivery of a drug to a patient over a 24-hour long period. Such a therapy schedule may be referred to as a daily therapy schedule in some instances. In other examples, a therapy schedule may be defined for period of time with an overall duration greater than or less than the twenty-four hours.

The total dose delivered to a patient, as defined by a therapy schedule, over the entire time period of the therapy schedule may be determined to evaluate whether or not an acceptable amount of therapeutic fluid will be delivered to a patient during the period of the therapy schedule. For example, for a daily therapy schedule, the total daily dose delivered to the patient over the 24-hour period may be determined. In some case, the total daily dose may be an acceptable amount to effectively treat a patient disorder. In other cases, the total daily dose may reflect the delivery of an excessive or insufficient amount of therapeutic fluid to a patient, which could result in an overdose or underdose, respectively, during the 24-hour period. In such a case, a clinician may adjust the therapy schedule as required for the total daily dose delivered to the patient to be an acceptable amount prior to programming the implantable medical fluid delivery device with the daily therapy schedule.

However, while the total dose delivered to a patient over the duration of a daily therapy schedule may be an acceptable amount, in some circumstances, there may be one or more discrete, shorter periods of time within the 24-hour period during which an excessive or insufficient dose may be programmed for delivery to a patient relative to the shorter period of time. Moreover, when a daily therapy schedule is repeated to define therapy over, e.g., a 48-hour period, there may be a period of time including a portion of the end of the first daily therapy schedule and a portion of the beginning of the following daily therapy schedule during which an unacceptable dose may be programmed for delivery to the patient. Such circumstances may be further complicated by the possibility for a supplemental bolus or other bolus to be delivered at one or more points in time outside that defined by a daily therapy schedule.

In accordance with one or more examples of the disclosure, a processor may be configured to evaluate a proposed therapy dosing program within one or more analysis windows that at least partially overlap the overall period of time of the proposed therapy dosing program. To evaluate the proposed therapy dosing program, the total dose defined for delivery within the analysis window may be determined, and then compared to a reference dosage, e.g., a reference dosage range acceptable for delivery to the patient over the duration of second time period. The total dosage delivered during the analysis window may be determined based only a therapy schedule of the proposed dosing program, or may be determined based on both on the therapy schedule in addition to possible supplemental boluses and/or other boluses that may be delivered during the analysis window. The possible delivery of supplemental and/or other boluses defined during the analysis window may also be defined by the proposed therapy dosing program. In some examples, based on the comparison, the processor may apply the proposed therapy dosage program for actual delivery of therapy to the patient by an implantable fluid delivery device, e.g., if the total dosage is determined to be within the reference dosage range. In some examples, an indicator indicative of the comparison may be presented to a user via a user interface, e.g., an indicator indicative of the total dosage being outside the reference dosage range.

As an illustration of one example of the disclosure, in the case of a proposed therapy dosing program including a therapy schedule that defines the delivery of a drug to a patient over the period of twenty-four hours, a processor of a device (e.g., a processor of an external programmer) may determine the total dose that would be delivered to the patient during one or more two-hour analysis windows overlapping at least a portion of the daily therapy schedule. The one or more total doses determined within the analysis windows may then each be compared to a reference dose. In some examples, the reference dose may include an acceptable total dose for delivery to a patient during a two-hour period of time. If the comparison indicates that the total dose determined for all of the analysis windows are acceptable (e.g., being within the reference dosage range), the processor may apply the proposed therapy dosing program to define therapy delivered to the patient at that time or some point in the future.

However, if the comparison indicates that the total dose determined for one or more of the analysis windows is unacceptable (e.g., being outside the reference dosage range), the processor may present an indicator via a user interface alerting a programming clinician or other user that the total dosage for one or more of the analysis window is outside the reference dosage range and may be undesired. In view of the indicator, the clinician may either modify the dosing program, replace the proposed dosing program with another dosing program, or proceed to program the implantable fluid delivery device with the dosing program (e.g., if he/she determines that there is actually no excessive/insufficient dose risk). In some examples, the programming device may display a graphical representation of the proposed therapy dosing program with one or more analysis window of interest highlighted to allow the clinician to visualize the proposed therapy and determine how to proceed.

FIG. 1 is a conceptual diagram illustrating an example of a therapy system 10, which includes implantable medical device (IMD) 12 and catheter 18. IMD 12 configured to deliver at least one therapeutic agent, such as a pharmaceutical agent, insulin, pain relieving agent, anti-inflammatory agent, gene therapy agent, or the like, to a target site within patient 16 via catheter 18, which is coupled to IMD 12. Therapy system 10 also includes external programmer 20, which wirelessly communicates with IMD 12 as needed, such as to provide or retrieve therapy information or control aspects of therapy delivery (e.g., modify the therapy parameters, turn IMD 12 on or off, and so forth). While patient 16 is generally referred to as a human patient, other mammalian or non-mammalian patients are also contemplated.

Generally, IMD 12 has an outer housing that is constructed of a biocompatible material that resists corrosion and degradation from bodily fluids, such as titanium or biologically inert polymers. IMD 12 may be implanted within a subcutaneous pocket close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent.

Catheter 18 may be coupled to IMD 12 either directly or with the aid of a catheter extension (not shown in FIG. 1). In the example shown in FIG. 1, catheter 18 traverses from the implant site of IMD 12 to one or more target sites proximate to spine 14. Catheter 18 is positioned such that one or more fluid delivery outlets of catheter 18 are proximate to the one or more target tissue or nerve sites within patient 16. IMD 12 delivers a therapeutic agent to the one or more target tissue or nerve sites proximate to spinal cord 14 with the aid of catheter 18. For example, IMD 12 may be configured for intrathecal drug delivery into the intrathecal space or epidural space surrounding spinal cord 14. The intrathecal space is within the subarachnoid space of spinal cord 14, which is past the epidural space and dura mater and through the theca of spinal cord 14. While the target site in FIG. 1 is proximate to spinal cord 14 of patient 16, other target sites are contemplated.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

Therapy system 10 may be used, for example, to reduce pain experienced by patient 16. IMD 12 may deliver one or more therapeutic agents to patient 16 according to one or more therapy dosing programs that set forth different therapy parameters, such as a therapy schedule specifying programmed doses, rates for the programmed dose, and specific times to deliver the programmed doses. The dosing programs may be may be a part of a program group for therapy, where the group includes a plurality of therapy schedules. In some examples, IMD 12 may be configured to deliver a therapeutic agent to patient 16 according to different therapy schedules on a selective basis. IMD 12 may include a memory to store one or more therapy dosing programs, instructions defining the extent to which patient 16 may adjust therapy parameters, switch between dosing programs, or undertake other therapy adjustments. Patient 16 or a clinician may select and/or generate additional dosing programs for use by IMD 12 via external programmer 20 at any time during therapy or as designated by the clinician.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 16 to view and modify therapy parameters. The clinician programmer may include additional or alternative programming features than the patient programmer. For example, more complex or sensitive tasks may only be allowed by the clinician programmer to prevent patient 16 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate through the user interface of programmer 20 and provide input.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may enter an application to become programmer 20 with a wireless adapter connected to the personal computer for communicating with IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy dosing program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

When programmer 20 is configured for use by the clinician, programmer 20 may be used to transmit initial programming information to IMD 12. This initial information may include hardware information for system 10 such as the type of catheter 18, the position of catheter 18 within patient 16, the type of therapeutic agent(s) delivered by IMD 12, a baseline orientation of at least a portion of IMD 12 relative to a reference point, one or more therapy dosing programs stored within IMD 12 or within programmer 20, and any other information the clinician desires to program into IMD 12.

A clinician may use programmer 20 to program IMD 12 with one or more therapy dosing programs that define the therapy delivered by IMD 12 to patient 16. During a programming session, the clinician may propose one or more therapy dosing programs that may provide effective therapy to patient 16. Programmer 20 may assist the clinician in the creation/identification of therapy dosing programs by providing a methodical system of identifying potentially beneficial therapy parameters.

A proposed therapy dosing may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. As noted above, a therapy dosing program may include one or more therapy schedules that define one or more programmed doses, where each dose includes a rate and duration of time over which to deliver the desired dose, for a predefined duration of time (e.g., a 24-hour period). A therapy dosing program may also include information regarding supplemental boluses, including information defining when the delivery of a supplemental bolus is authorized.

In accordance with the techniques described herein, one or more processors of programmer 20, IMD 12, and/or other device may be configured to evaluate a proposed therapy dosing program prior to being applied by IMD 12 to define therapy delivered to patient 16. For example, for a proposed therapy dosing program defining therapy over a first period of time, such processor(s) may determine the total dose defined for delivery by the therapy dosing program for one or more analysis windows that overlap at least a portion of the first duration of time. The total dose determined for each analysis window may be compared to a reference dosage defined for the time period of the analysis window. In some examples, based on the comparison, the one or more processors of the device(s) may determine apply the proposed therapy dosing program to define therapy actually delivered to patient 16 via IMD 12.

Whether programmer 20 is configured for clinician or patient use, programmer 20 may communicate to IMD 12 or any other computing device via wireless communication. Programmer 20, for example, may communicate via wireless communication with IMD 12, e.g., using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and another programmer via remote telemetry techniques known in the art, communicating via a local area network (LAN), wide area network (WAN), public switched telephone network (PSTN), or cellular telephone network, for example.

In applications of therapy system 10, catheter 18 may be configured to deliver therapy agents from IMD 12 to one or more target sites of patient 16. In some examples, catheter 18 may be positioned to deliver one or more therapeutic agents to the intrathecal space or other sites proximate to the spinal cord of a patient, e.g., to influence nerves of the spinal cord. In some examples, the target delivery site may be proximate to different types of tissues including, e.g., sacral, pudendal or perineal nerves, organs, muscles or muscle groups. As another example, catheter 18 may be positioned to deliver a therapeutic agent to a deep brain site, vasculature, or within the heart (e.g., intraventricular delivery of the agent). Delivery of a therapeutic agent within the brain may help manage any number of disorders or diseases. Example disorders may include depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

Examples of therapeutic agents that IMD 12 may be configured to deliver include, but are not limited to, insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics.

Figure 2:
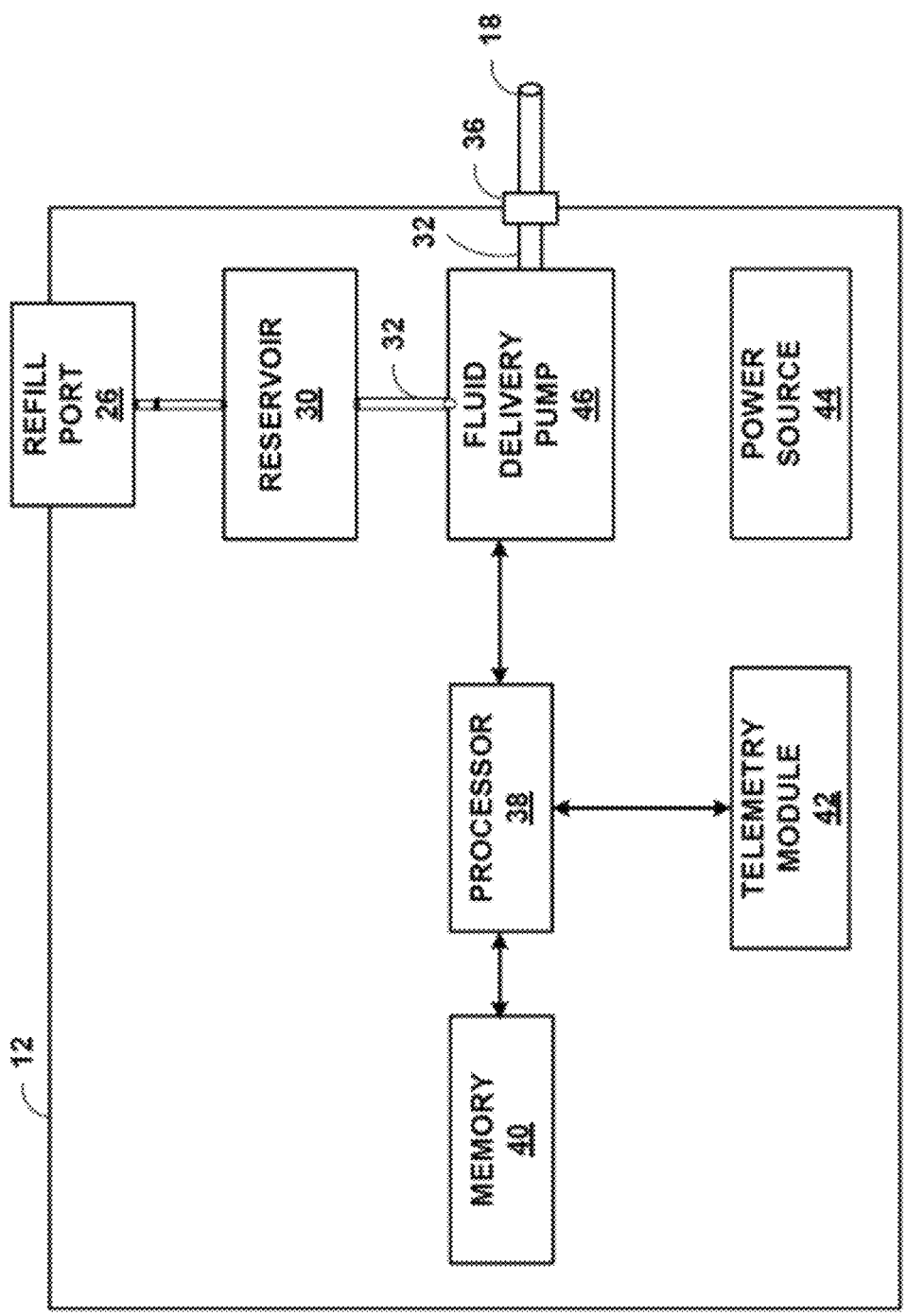
FIG. 2 is functional block diagram illustrating an example of an implantable fluid delivery device.

FIG. 2 is a functional block diagram illustrating components of an example of IMD 12, which includes refill port 26, reservoir 30, processor 38, memory 40, telemetry module 42, power source 44, fluid delivery pump 46, internal tubing 32, and catheter access port 36. Fluid delivery pump 46 may be a mechanism that delivers a therapeutic agent in some metered or other desired flow dosage to the therapy site within patient 16 from reservoir 30 via the catheter 18. Refill port 26 may comprise a self-sealing membrane to prevent loss of therapeutic agent delivered to reservoir 30 via refill port 26. After a delivery system, e.g., a hypodermic needle, penetrates the membrane of refill port 26, the membrane may seal shut when the needle is removed from refill port 26.

Internal tubing 32 is a segment of tubing that runs from reservoir 30, around or through fluid delivery pump 46, to catheter access port 36. In one example, fluid delivery pump 46 may be a squeeze pump that squeezes internal tubing 32 in a controlled manner, e.g., such as a peristaltic pump, to progressively move fluid from reservoir 30 to the distal end of catheter 18 and then into the patient according to parameters specified by a set of program information. Fluid delivery pump 46 may, in other examples, comprise an axial pump, a centrifugal pump, a pusher plate, a piston-driven pump, or other means for moving fluid through internal tubing 32 and catheter 18.

Processor 38 controls the operation of fluid delivery pump 46 with the aid of instructions associated with program information that is stored in memory 40. For example, the instructions may define dosing programs that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of the dosage rate at which the fluid is delivered. The therapy programs may also include other therapy parameters, such as the frequency of bolus delivery, the type of therapeutic agent delivered if IMD 12 is configured to deliver more than one type of therapeutic agent), and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 40 may include any volatile or non-volatile media, such as a random access memory (RAM), read only memory (ROM), non-volatile RAM (NVRAM), electrically erasable programmable ROM (EEPROM), flash memory, and the like. As mentioned above, memory 40 may store program information including instructions for execution by processor 38, such as, but not limited to, therapy programs, historical therapy programs, timing programs for delivery of fluid from reservoir 30 to catheter 18, and any other information regarding therapy of patient 16. A program may indicate the bolus size or flow rate of the drug, and processor 38 may accordingly deliver therapy. Memory 40 may include separate memories for storing instructions, patient information, therapy parameters (e.g., grouped into sets referred to as "dosing programs" or "therapy dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 40 stores program instructions that, when executed by processor 38, cause IMD 12 and processor 38 to perform the functions attributed to them in this disclosure.

Memory 40 may be considered, in some examples, a non-transitory computer-readable storage medium comprising instructions that cause one or more processors, such as, e.g., processor 38, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 14, and moved to another device. In certain examples, a non-transitory storage medium may store data that can, over time, change (e.g., in RAM).

Telemetry module 42 in IMD 12, as well as telemetry modules in other devices described herein, such as programmer 20, may accomplish communication by RF communication techniques. In addition, telemetry module 42 may communicate with programmer 20 via proximal inductive interaction of IMD 12 with external programmer 20. Accordingly, telemetry module 42 may send information to external programmer 20 on a continuous basis, at periodic intervals, or upon request from the programmer. Processor 38 controls telemetry module 42 to send and receive information. Wireless telemetry may be accomplished by RF communication or proximal inductive interaction of IMD 12 with external programmer 20.

Power source 44 delivers operating power to various components of IMD 12. Power source 44 may include a small rechargeable or non-rechargeable battery and a power generation circuit to produce the operating power.

Figure 3:
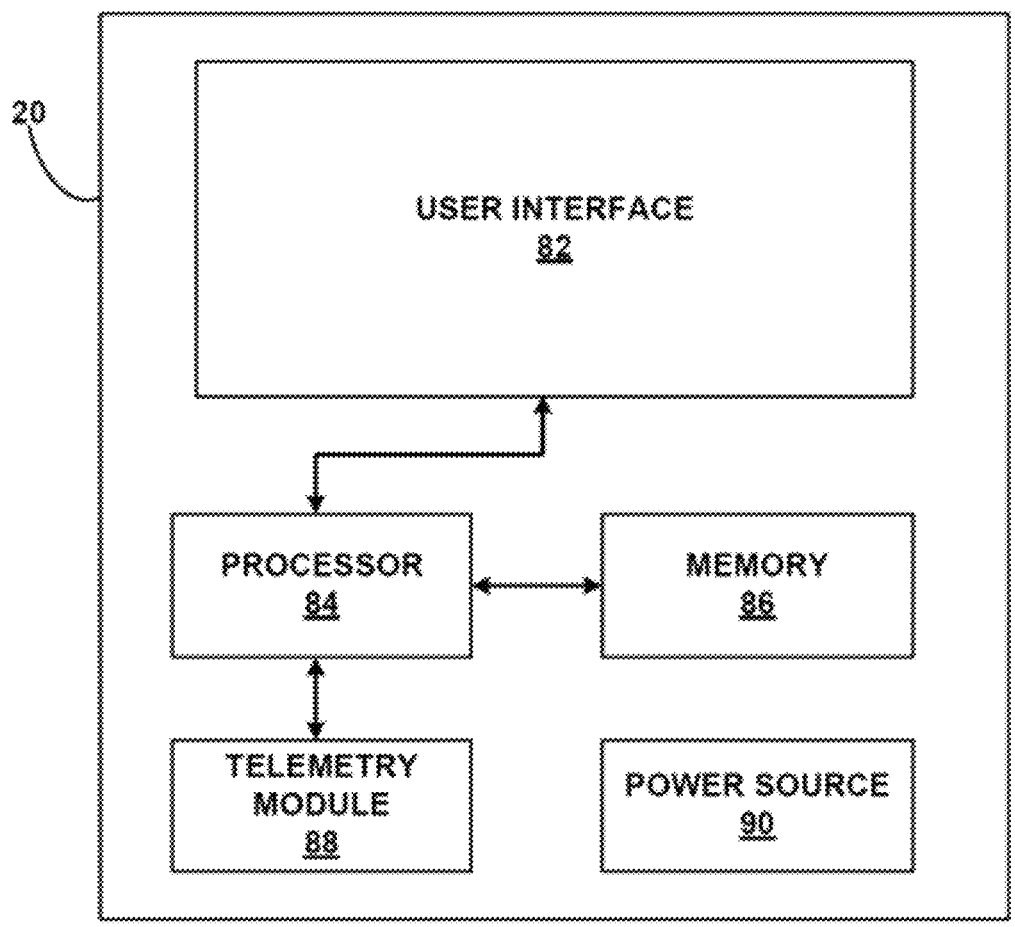
FIG. 3 is a functional block diagram illustrating example components of an external programmer for an implantable medical device.

FIG. 3 is a functional block diagram illustrating various components of an external programmer 20 for IMD 12. As shown in FIG. 3, external programmer 20 includes processor 84, memory 86, telemetry module 88, user interface 82, and power source 90. A clinician or patient 16 interacts with user interface 82 in order to manually change the parameters of a therapy dosing program, change therapy dosing programs within a group of programs, view therapy information, view historical therapy regimens, establish new therapy regimens, or otherwise communicate with IMD 12 or view programming information.

User interface 82 may include a screen and one or more input buttons that allow external programmer 20 to receive input from a user. Alternatively, user interface 82 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible indications of dosing program parameters or operational status, a display screen may suffice. For audible and/or tactile indications of dosing program parameters or operational status, programmer 20 may further include one or more audio speakers, voice synthesizer chips, piezoelectric buzzers, or the like.

Processor 84 controls user interface 82, retrieves data from memory 86 and stores data within memory 86. Processor 84 also controls the transmission of data through telemetry module 88 to IMD 12. The transmitted data may include therapy dosing program information specifying various drug delivery program parameters. Memory 86 may include operational instructions for processor 84 and data related to therapy for patient 16. In some examples, memory 86 may store information defining reference dosages defined for respective analysis windows and other information that may be used by processor 84 to evaluate proposed therapy dosing programs according to one or more examples of the disclosure.

User interface 82 may be configured to present dosing program information to the user. User interface 82 enables a user to program IMD 12 in accordance with one or more dosing programs, e.g., programs that define a therapy schedule for delivering programmed doses of fluid, a priming bolus, a therapeutic bolus, a bridging process, or similar information. A user such as a clinician, physician or other caregiver may input patient information, drug information, therapy delivery schedules, priming information, bridging information, drug/IMD implant location information, or other information to programmer 20 via user interface 82. In addition, user interface 82 may display dosing program information as graphical bar graphs or charts, numerical spread sheets, or in any other manner in which information may be displayed.

Telemetry module 88 allows the transfer of data to and from IMD 12. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Power source 90 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

As described above, some examples of the disclosure relates to techniques for evaluating a proposed therapy dosing program. In some examples, to evaluate a proposed therapy dosing program, the total dose proposed for delivery during each of one or more discrete periods of time (or "analysis windows") at least partially overlapping the overall period of time for which a therapy dosing program defines therapy may be determined. Once determined, such total doses may be compared to a reference dose defined for the duration of the analysis window. Based on the comparison, a proposed therapy program may be, for example, applied to define therapy actually delivered to patient 16 via IMD 12, or rejected.

Figure 4:
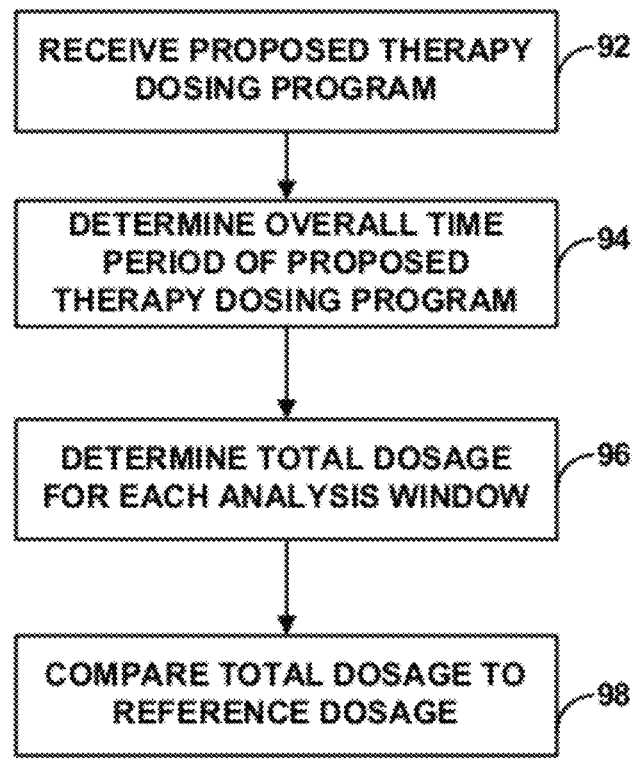
FIG. 4 is a flow diagram illustrating an example technique for evaluating a proposed therapy program.

FIG. 4 is a flow diagram illustrating one example technique for evaluating a proposed therapy dosing program. For purposes of illustration, the example technique will be described with regard to therapy system 10 (FIG. 1), although other therapy systems are contemplated. The example technique of FIG. 4 may be implemented prior to applying a proposed therapy dosing program to define therapy actually delivered to patient 14 via IMD 12. For example, such an example technique may be utilized during a programming session during which one or more therapy dosing programs are defined by a clinician for controlling the therapy delivered by IMD 12 to patient 16 once applied. In this manner, such an example technique may be used to screen a proposed therapy program to identify windows of time within the overall time duration of the proposed therapy program where an undesirable amount (e.g., excessive or insufficient) could potentially be administered to patient 16 if the therapy dosing program were to be applied to define therapy delivered via IMD 12.

In one example, a single proposed therapy program may be evaluated by the example technique of FIG. 4. In other examples, multiple proposed therapy dosing programs proposed to be delivered consecutively may be evaluated using such a technique, with the analysis window overlapping at least a portion of each of the proposed therapy dosing programs. For example, as described with regard to FIG. 7 below, for two proposed therapy dosing programs delivered consecutively, such an evaluation may be used to identify time periods during which a potentially unacceptable dose may be programmed for delivery to the patient resulting from the proposed combination of first and second therapy dosing programs. This may be the case even if there are no time periods during the first therapy dosing program and the second therapy dosing program, when evaluated individually, for which the total dosage within the analysis window is outside that of the reference dosage range.

For ease of illustration, the example technique of FIG. 4 is described with regard to processor 84 of external programmer 20 receiving and analyzing a proposed therapy dosing program. However, examples are not limited to such a configuration, and processor of one or more devices may be utilized to perform all or portions of the techniques in addition to or in lieu of that of processor 84 of programmer 20. For example, processor 38 of IMD 12 may perform all or a portion of the example technique of FIG. 4 in combination with or instead of processor 84.

As shown in FIG. 4, processor 84 receives information defining a proposed therapy dosing program (92). The proposed therapy program received by processor 84 may be defined, for example, by a clinician or other user during or prior to the programming session. After receiving the information defining a proposed therapy dosing program (92), processor 84 may determine the overall time period of the proposed therapy dosing program (94). The overall or total time period of a proposed therapy dosing program may be equal to that of the total time elapsed from the first point at which a rate is defined by a therapy schedule to the last point that a rate is defined by a therapy schedule. For example, a proposed therapy dosing program that includes a daily therapy schedule, processor 84 may determine the overall time period of the proposed therapy dosing program is twenty-four hours.

After receiving the proposed therapy dosing program (92) and determining the overall time period of the proposed therapy dosing program (94), processor 84 may determine the total dosage proposed for delivery to patient 16 within each of one or more analysis windows (96) for the proposed therapy dosing program. The one or more analysis windows used by processor 84 may correspond to a substantially continuous period of time that at least partially overlaps the overall time period of the proposed therapy dosing program. In some examples, the analysis window may be a period of time substantially entirely within the overall time period of the proposed therapy dosing program. For example, for a therapy dosing program defining therapy delivery over a twenty-four hour period of time, the analysis window may be defined by a time period of less than twenty-four hours (e.g., a two hour analysis window). In the case of a two hour analysis window, as one example, processor 84 may evaluate the proposed therapy dosing program temporally in two hour blocks of time overlapping the overall time period. Such an example is described further below with regard to FIG. 5. In some examples, the duration of the analysis window is less than the duration of the overall time period of the proposed therapy dosing program.

Processor 84 may determine the total dosage within the analysis window (96) based on the duration and rate of each dose defined by the proposed therapy dosing program during the period of time being evaluated. In the case of a therapy dosing program represented as a plot of rate versus time, the total dosage within an analysis window would be approximately equal to the total area under the plot during the particular time period of the analysis window.

Processor 84 may determine that total dosage for a single analysis window or multiple different analysis windows at least partially (e.g., substantially entirely) overlapping the overall time period of the proposed therapy dosing program (96). For each analysis window, processor 84 may compare the total dosage to a reference dosage (98). In some examples, the reference dosage may generally define the dosage that is acceptable for delivery to a patient in view of the duration of the analysis window. In the example, of FIG. 4, the reference dosage used to compare to the total dosage for each analysis window includes a range of dosage values, the bounds of which may be defined by a lower threshold dosage value and an upper threshold dosage value. In some examples, the lower threshold dosage value may be zero or some value other than zero. In some examples, the upper threshold value may be a specific value or defined as any value greater than zero. In some examples, the reference dosage may be defined as zero, e.g., for cases in which it is desired for no dosage to be delivered to a patient over the duration of the analysis window.

Figure 9:
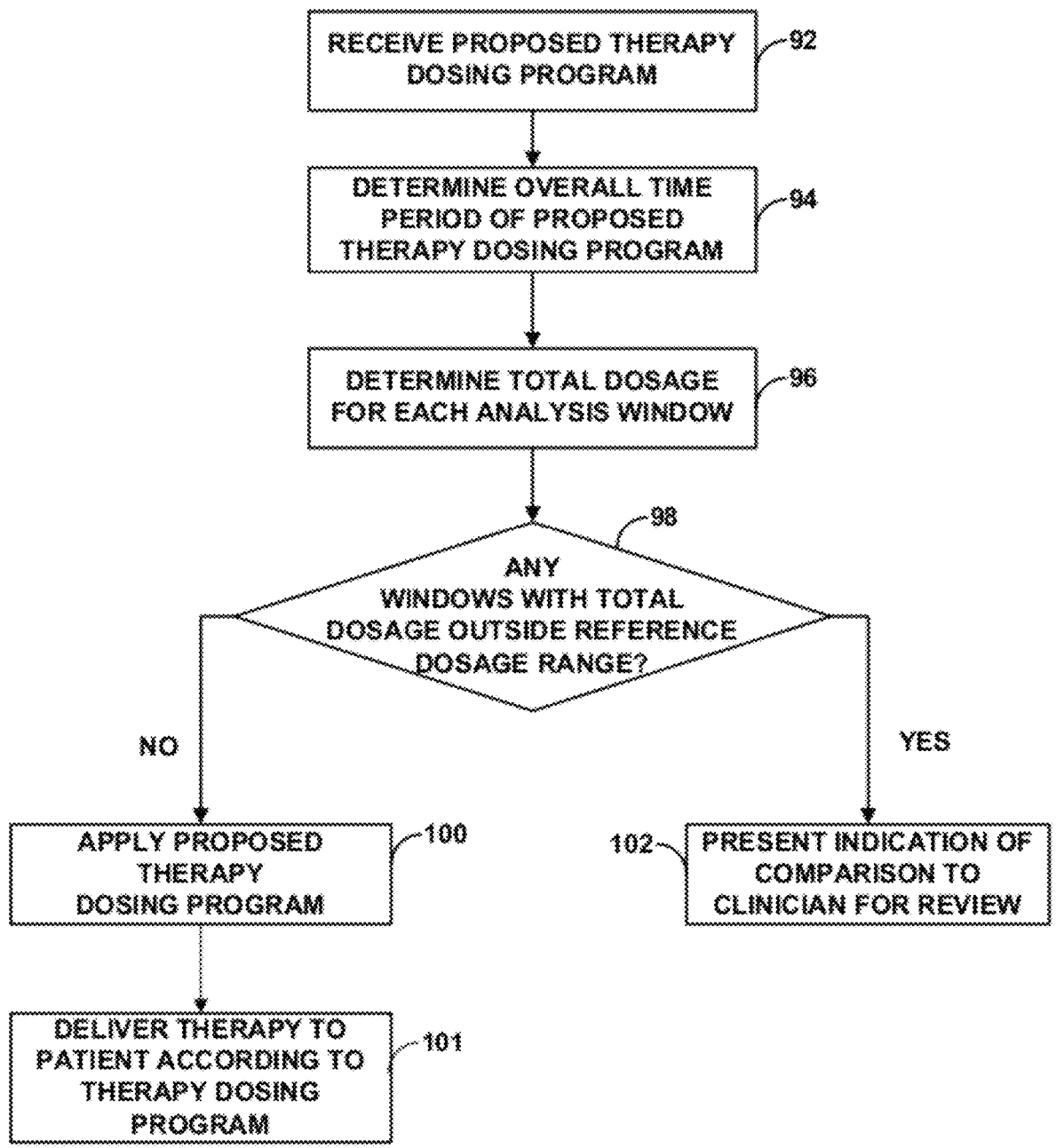
FIG. 9 is a flow diagram illustrating another example technique for evaluating a proposed therapy program.

As will be described further below, processor 84 may take any of a variety of steps based on the comparison (98). FIG. 9 is a flow chart illustrating one example for evaluating a proposed therapy program. As described with regard to FIG. 4, after receiving the proposed therapy dosing program (92)

and determining the overall time period of the proposed therapy dosing program (94), processor 84 may determine the total dosage proposed for delivery to patient 16 within each of one or more analysis windows (96) for the proposed therapy dosing program. Processor 84 may then compare each of the determined total dosages to the reference dosage range (98).

If the total dosage determined to each analysis window is within the reference dosage range, processor 84 may apply the proposed therapy program (100), e.g., by transmitting the proposed therapy dosing program to IMD 12 via telemetry module 88 (FIG. 3). Processor 38 of IMD 12 may store the proposed therapy program 40 in memory 40, and access the proposed therapy program 40 to control the delivery of the therapeutic agent to patient 16, e.g., to treat a patient condition. In particular, as shown in FIG. 4, processor 38 may control pump 46 to deliver therapy according to the therapy dosing program (101). In some examples, processor 84 may automatically apply the proposed therapy program based on the comparison (98), or may do so after receiving approval from a user via user interface 82 to apply the program. In some example, such user input is prompted in combination with an indicator indicating the results of the comparison displayed via user interface 82. Such an indicator may be presented to a user via user interface 82 even if user approval for application of the proposed therapy program is not required.

As another example, if the total dosage determined for any of the analysis window is outside the reference dosage range (above or below the reference dosage range), processor 84 may not directly apply the proposed therapy dosing program. By not applying the proposed therapy dosing program, processor 84 may prevent, at least temporarily, IMD 12 from using the proposed therapy dosing program to define therapy actually delivered to patient 16. As shown in FIG. 9, in some examples, processor 84 may generate an alert, message or other indicator (e.g., via user interface 82) indicating to the user that the proposed therapy program defines a total dosage within one or more analysis windows that is outside the reference dosage range rather than transmitting the proposed therapy program to IMD 12 (102). Based on such an indicator, a user may decide, for example, to modify the proposed therapy dosing program, replace the proposed therapy, dosing program with another dosing program, or proceed to program the implantable fluid delivery device with the dosing program (e.g., if the user determines that there is actually no excessive/insufficient dose risk).

FIG. 5 is a conceptual diagram illustrating example representation of an example therapy defined by an example therapy dosing program. For purposes of illustration, the example technique of FIG. 4 will be further described with regard to the proposed therapy program represented by FIG. 5. As shown, the overall time period of the proposed dosing program represented in FIG. 5 is approximately twenty-four hours. For reference, time is shown on the horizontal axis running from approximately midnight to midnight. However, the proposed therapy dosing program could be used by IMD 12 to define the delivery of therapy to patient 16 for any twenty-four hour period. Moreover, other example proposed therapy dosing programs may define overall time periods that are less or greater than twenty-four hours.

As described above, a proposed therapy dosing program may include both a therapy schedule as well an information regarding the authorization for the delivery of supplemental boluses (e.g., a patient request supplemental bolus) and/or any other type bolus. In the example of FIG. 5, solid line 104 represents the rate and duration defined by a therapy schedule of the proposed therapy dosing program. Dashed line 106 represents the rate and duration in the event that the therapy schedule is combined with a potential supplemental bolus. As such, the difference in rate between line 104 and line 106 represents the increase in rate when a supplemental bolus is delivered to patient 16 outside of the therapy schedule. While in practice, it may not be possible to deliver a supplemental bolus throughout the entire twenty-four hour time period (e.g., due to supplemental bolus authorization lock-outs), processor 84 may use such an increased rate when evaluating a proposed therapy dosing program as the particular time at which a supplemental bolus is delivered, e.g., in response to a patient request, may not be known when the proposed therapy dosing program in being evaluated.

Processor 84 may utilize analysis window 108 to evaluate the proposed therapy dosing program of FIG. 5. As shown, analysis window 108 has a duration of approximately two hours, although other analysis windows with durations other than two hours are contemplated. The duration of analysis window 108 may be adjustable by a user, such as a clinician or other caregiver, during a programming session and/or may be a preprogrammed value. In some examples, the duration of an analysis window may be some default value based on the overall duration of a proposed therapy program. For example, the duration of analysis window 108 may be some percentage (e.g., approximately 10 percent) of the overall duration of a proposed therapy program.

According to the example of FIG. 4, after receiving the proposed therapy dosing program 92, processor 84 may determine the total dosage proposed for delivery to patient 16 via IMD 12 during analysis window 108 (96), and then compare the total dosage proposed for delivery to a reference dosage. The reference dosage may be defined to correspond to the duration of analysis window 108, which in the case of the example of FIG. 5 is approximately two hours. In such an example, the reference dosage used by processor 84 may generally reflect a total dosage over two hours (or whatever the duration of the analysis window) that is believed to effectively treat the condition of patient 16 but not result in any undesirable side effects due to excessive or insufficient delivery of therapeutic fluid to patient 16 over two hours. Such a reference dosage may be patient and/or drug specific, and may be defined by a clinician and/or supplier of the therapeutic fluid delivered to patient 16 via IMD 12. A clinician may manually input the reference dosage value or range or such a reference dosage may be automatically set. As described above, a reference dosage range may be defined in terms of an upper limit, a lower limit, or both for the duration of the analysis window.

In some examples, a reference dosage may be provided on labeling or other material provided by a medical device manufacturer for a certain therapy (e.g. for pain therapy) or "on label" for, e.g., delivery of Morphine (as an alternate e.g. for Baclofen for spasticity). Alternatively or additionally, a clinician may develop his/her own protocols governing what he/she considers a "reasonable" dosage range or approach to dosing as a broader policy (applicable to all patients). A clinician may make patient specific decisions, e.g., based on the history and status of the patient (e.g. in a cancer pain case, as the patient has increasing tolerance over time, a reference dosage range may increase over time) with regard to reference dosage. Alternatively or additionally, a certain set of guidelines published by a group of experts (such as in a journal or the proceedings of a conference) may be used to define the reference dosage for a particular time period. Alternatively or additionally, a medical device manufacturer or another party familiar with the clinical use of such systems may empirically model the "normal" range of difference in dosage between any given time hour period (e.g., two hours) and a patients average daily rate (perhaps even for a specific drug or admixture), and then provide guidance to a user at to that normal range of change (e.g., a certain percentage or number of mg (or other unit) of drug increase/decrease).

In some examples, it may be possible to identify an approximate mathematical relationship which takes such factors as the daily dose, drug information and/or duration of a shorter analysis window as inputs and provides a reasonable range of change output to define a reference dosage range. Even if such an equation was defined to be fairly conservative, it may still pick up certain kinds of dosing programming errors (such as, e.g., defining a patient bolus or step that has a much higher dose than it was intended to because of order of magnitude errors).

As the reference dosage values may be specific to the duration of analysis window, the reference dosage for an analysis window of a first duration may be different than the reference dosage for an analysis window of a second duration.

In some cases, the reference dosage may be defined based at least in part on the total dosage delivered over the entire time period of the proposed therapy. For example, the reference dosage may be defined as the percentage of the total dosage proposed for delivery over the entire time period of the proposed therapy dosing program, where the percentage is approximately equal to the percentage that the duration of the analysis window is of the overall duration of the proposed therapy dosing program. For example, in the case of the example shown in FIG. 5, the reference dosage value may be defined as approximately 8.34% (or approximately $1/12$) of the total dosage proposed for delivery over the entire time period of the therapy dosing program. In FIG. 5, the total dosage proposed for delivery over the entire time period, according to only the proposed therapy schedule, may be approximately equal to the total area under line 104. Alternatively, the total dosage for delivery over the entire time period, according to the proposed therapy schedule in combination with the potential for delivery of one or more supplemental boluses, may be approximately equal to the total area under line 106. In either case, such a value may be used alone as the reference dosage value or may be used to define a referenced dosage range using such a value as a baseline. For example, the reference dosage range may be defined as any dosage within, for example, 25% of the dosage value (above and/or below) calculated as described above.

Regardless of the particular reference dosage defined for the duration of analysis window 108, processor 84 may compare the total dosage proposed for delivery within analysis window 108 to the reference dosage (98). As described above, in some examples, processor 84 may determine whether to apply the proposed therapy program based on the comparison. In particular, if the reference dosage is defined by a range of values that are acceptable for delivery to patient 16 over the duration of analysis window 108, processor 84 may apply the proposed therapy program if the total dosage proposed for delivery during analysis window 108 is within the range. After being applied, processor 38 may deliver therapy to patient 16 according to the therapy dosing program. In some cases, the proposed therapy may undergo further evaluation prior to actually being utilized by processor 38 to control the delivery of therapeutic fluid to patient 16 via IMD 12.

In some examples, when a proposed therapy program has been applied by processor 84, processor 84 may transmit information defining the proposed therapy dosing program to IMD 12. The proposed therapy dosing program may then be stored in memory 40, and processor 38 may use the proposed therapy program to control the delivery of therapeutic fluid to patient 16 at some later point in time. Alternatively, the therapy dosing program may be stored in memory 86, and processor 38 of IMD 12 may access the therapy dosing program via telemetry as needed to control the delivery of therapeutic fluid to patient 16. In some examples, only proposed therapy dosing programs that have been applied by processor 84 after being evaluated according to the example technique of FIG. 4, or some variations thereof, may be used by IMD 12 to define therapy delivered to patient 16 via IMD 12.

In some examples, if processor 84 determines that the total dosage within analysis window 108 is outside the reference dosage range, processor 84 may not directly apply the proposed therapy dosing program. If processor 84 does not apply a proposed therapy dosing program, the proposed therapy dosing program may not be used to define therapy delivered to patient 16 via IMD 12. In some examples, processor 84 may generate and display an indicator via user interface 82 indicating to a clinician or other user that a proposed therapy dosing program includes a total dosage during an analysis window that is inconsistent with the reference dosage (e.g., outside the reference dosage range). In this manner, the user may be informed of the potential issue with the proposed therapy dosing program, and decide what modifications, if any, should be made in view of the rejection of the proposed therapy dosing program.

In some examples, a clinician may input a new, proposed therapy dosing program in place of a proposed therapy dosing program that has been rejected, in which case processor 84 may evaluate the new therapy dosing program using substantially the same technique that resulted in the rejection of the prior proposed therapy dosing program. Alternatively, a clinician may input one or more modifications to the proposed therapy dosing program, e.g., via user interface 82 (FIG. 3). For instance, a clinician may adjust the rate (e.g., increase or decrease) and/or duration of the delivery defined by a therapy schedule during at least a portion of the time period for which the total dosage within analysis window 108 was determined to be outside the reference dosage range. Alternatively or additionally, a clinician may adjust the authorization for supplemental boluses or other supplemental boluses that may be delivered during the time period of the therapy schedule. In any case, after the rejected proposed therapy dosing program has been modified, processor 84 may again evaluate the proposed therapy dosing program using substantially the same technique. This process may be repeated until processor 84 determines that there is not an analysis window during which the total dosage is outside the reference dosage. Processor 84 may then apply the proposed therapy dosing program (100), and the proposed therapy dosage program may be used by processor 38 to define the delivery of therapy to patient 16 via IMD 12 (101).

While the example of FIG. 5 illustrates analysis window 108 as overlapping a single period of time (i.e., from about 7:45 am to about 9:45 am) of the proposed therapy dosing program, analysis window 108 may be adjusted to overlap any period of time at least partially within the proposed therapy dosing program. Moreover, analysis window 108 may be moved, in a conceptual sense, to overlap a plurality different periods of time at least partially within the proposed therapy dosing program. In such a case, processor 84 may determine the total dosage proposed for delivery to patient 16 for each of multiple different two hour periods of time (or, more generally, the duration of analysis window 108) overlapping the proposed therapy dosing program, and compare the total dosage determined for each time period to the reference dosage defined for the duration of analysis window 108. In some examples, a clinician may direct the position of window 108 over a proposed therapy dosing window, e.g., based on time periods thought to be of interest. Additionally or alternatively, processor 84 may automatically or semi-automatically evaluate all or a portion of proposed therapy dosing program when received.

As an illustration, in the example of FIG. 5, processor 84 may determine the total dosage proposed for delivery for each of the time periods from 12 am to 2 am, 2 am to 4 am, 4 am to 6 am, and so forth (96), and compare the total dosage determined for each time period to the reference dosage (98) as described above. In some examples, processor 84 may apply the proposed therapy program based on the plurality of comparisons. In some examples, the results of the comparison may be presented to user for evaluation. For example, if processor 84 determines that one or more of the total dosages are outside the reference dosage range, processor 84 may alert a user that the total dosage of one or more analysis windows of the proposed therapy dosing program is outside the reference dosage range. Alternatively, if processor 84 determines that none of the total dosages are outside the reference dosage range, processor 84 may apply the proposed therapy dosing program to define therapy actually delivered to patient 16 via IMD 12 or present the results of the comparison to a user and prompt the user to confirm that the therapy dosing program should be applied.

Processor 84 may use one or more analysis windows in such a fashion to evaluate a portion or substantially all of a proposed therapy dosing program. In some examples, processor 84 may analyze substantially all of the overall time period of a proposed therapy dosing program by way of a plurality analysis windows having a duration of less than the overall time period of the proposed therapy dosing program. In this sense, analysis window 108 may moved or "swept" over the entire time period of the proposed therapy program to detect any periods of time during which the total dosage delivered to patient 16 would be outside the reference dosage range defined for the duration of analysis window 108.

In cases in which processor 84 analyzes a proposed therapy dosing program by determining a total dosage during each of a plurality of analysis windows, the increments of offset between respective analysis windows may be less than the duration of the analysis windows. For example, for the two hour analysis window 108 in FIG. 5, processor 84 may determine a total dosage for analysis windows with the start of each window offset by, for example, approximately 15 minutes (12:00 am, 12:15 am, 12:30 am, and so forth). In other examples, the increments of offset between respective analysis windows may be greater than or approximately equal to the duration of the analysis windows.

In some examples, processor 84 may incrementally move analysis window 108 over all or a portion of a propose therapy dosing program (e.g., in approximately 1 minutes increments). In some examples, rather than analyzing substantially the entire duration of a proposed therapy program, processor 84 may identify particular areas of interest of a therapy dosing program to evaluate and/or periods during which it is unlikely that the therapy dosing program defines an overall dosage that is not outside a reference dosage range for the analysis window. For example, if the duration of analysis window 108 is relatively small and window 108 fits entirely within a period of time where the rate was constant (e.g., during the middle of a step or patient bolus), then all the windows positions within that constant rate would be the same. In such a case, processor 84 may only evaluate the boundaries with other rates and once at some period of time where the rate is constant. In some examples, the boundaries between relatively long steps may be used to target the period of time evaluated by analysis window 108. For example, if the window is small enough relative to the constant rate periods that it can only cover one boundary at a time, then processor 84 may determine, based on which of the two rates is higher and whether over or under dose is of interest (or both in two separate passes), which temporal position will produce the "worse" dosage, and not calculate the boundary or the step/period corresponding to the "better" dose windows.

In addition to adjusting the time period of a proposed therapy dosing program being analyzed by processor 84, the duration of analysis window 108 may also be adjusted. In some examples, all or portions of a proposed therapy dosing program may be analyzed by processor 84 with multiple analysis windows each having different durations. In some examples, processor 84 may evaluate substantially all of the time period of a proposed dosing program (approximately twenty-four in the example of FIG. 5) with a plurality of analysis windows each having a first duration. Processor 84 may also evaluate substantially all of the time period of a proposed dosing program (approximately twenty-four in the example of FIG. 5) with a plurality of analysis windows each having a second duration different than the first duration.

FIGS. 6A-6F are conceptual diagrams illustrating an example representation of an example therapy defined by an example therapy dosing program. The examples of FIG. 6A-6F are used to illustrate examples in which processor 84 evaluates "worst" case scenarios for proposed therapy dosing programs. Processor 84 may identify the "worst" case scenarios automatically according to the bolus authorization information and therapy schedule defined by a proposed therapy dosing program.

In FIGS. 6A-6F, the therapy dosing schedule of the proposed therapy dosing program is substantially similar to that of FIG. 5. As shown, the overall time period of the proposed dosing program represented in FIG. 6 is approximately twenty-four hours. For reference, again, time is shown on the horizontal axis running from approximately midnight to midnight. However, the proposed therapy dosing program could be used by IMD 12 to define the delivery of therapy to patient 16 for any twenty-four hour period. Moreover, other example proposed therapy dosing programs may define overall time periods that are less or greater than twenty-four hours.

Figure 6A:
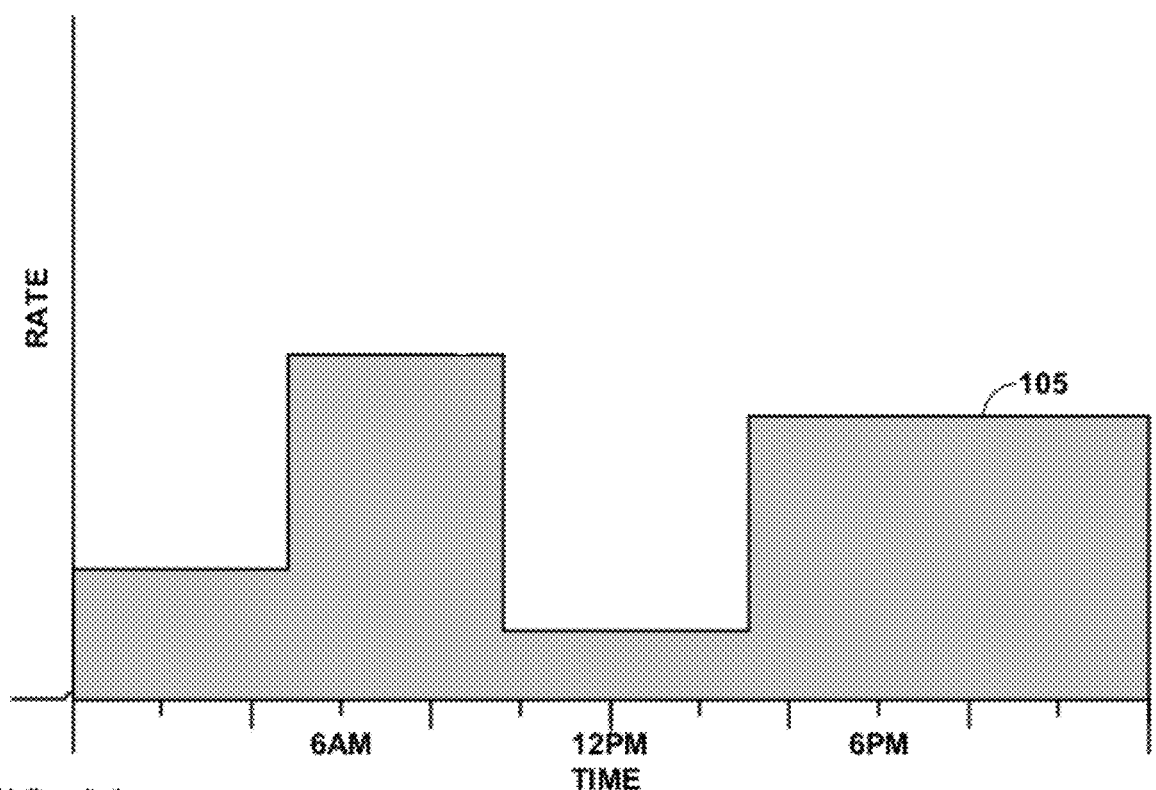
FIGS. 6A-6F are conceptual diagrams illustrating an example representation of an example therapy defined by an example therapy dosing program.

In the example of FIG. 6A, solid line 105 represents the rate and duration defined by a therapy schedule of the proposed therapy dosing program. Box 107 (shown in FIGS. 6B-6F) represents the rate and duration of a single bolus authorized for delivery by the proposed therapy dosing program. Unlike that shown in FIG. 5, such a bolus is shown as being defined by a fixed rate and period of time, rather than a percentage increase relative to the therapy schedule rate.

Figure 6B:
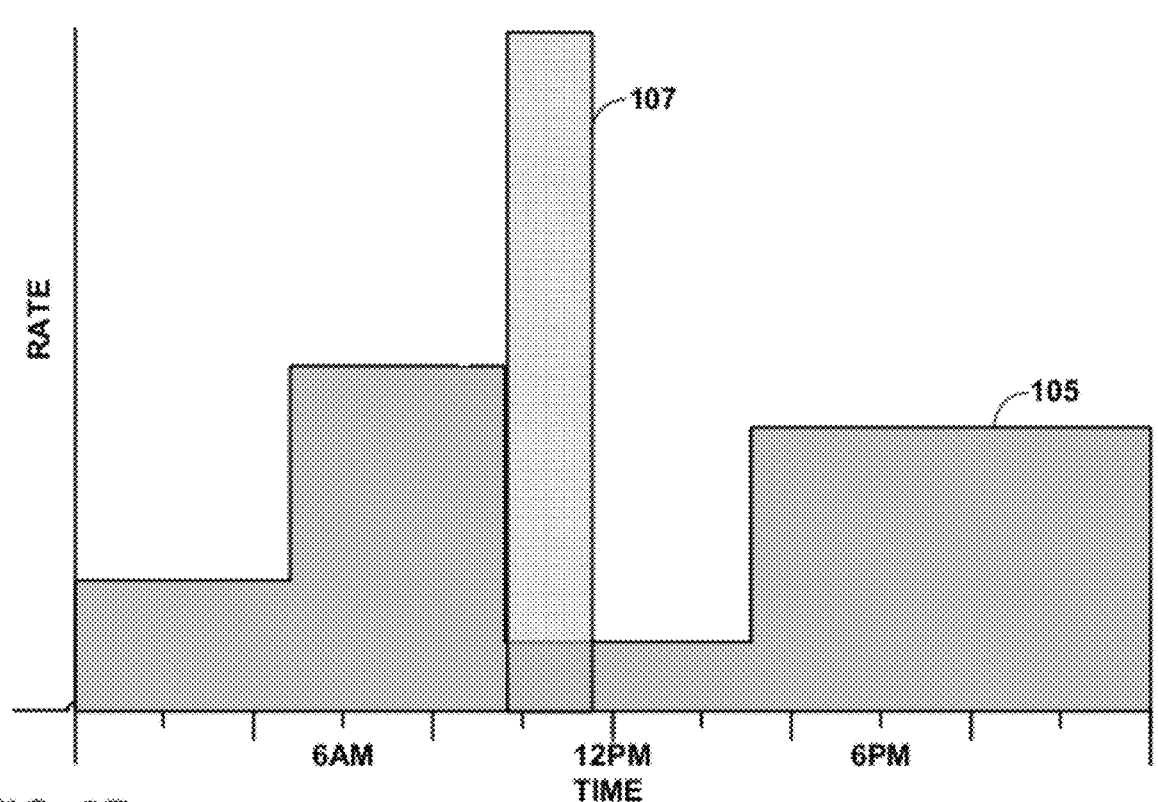
Figure 6C:
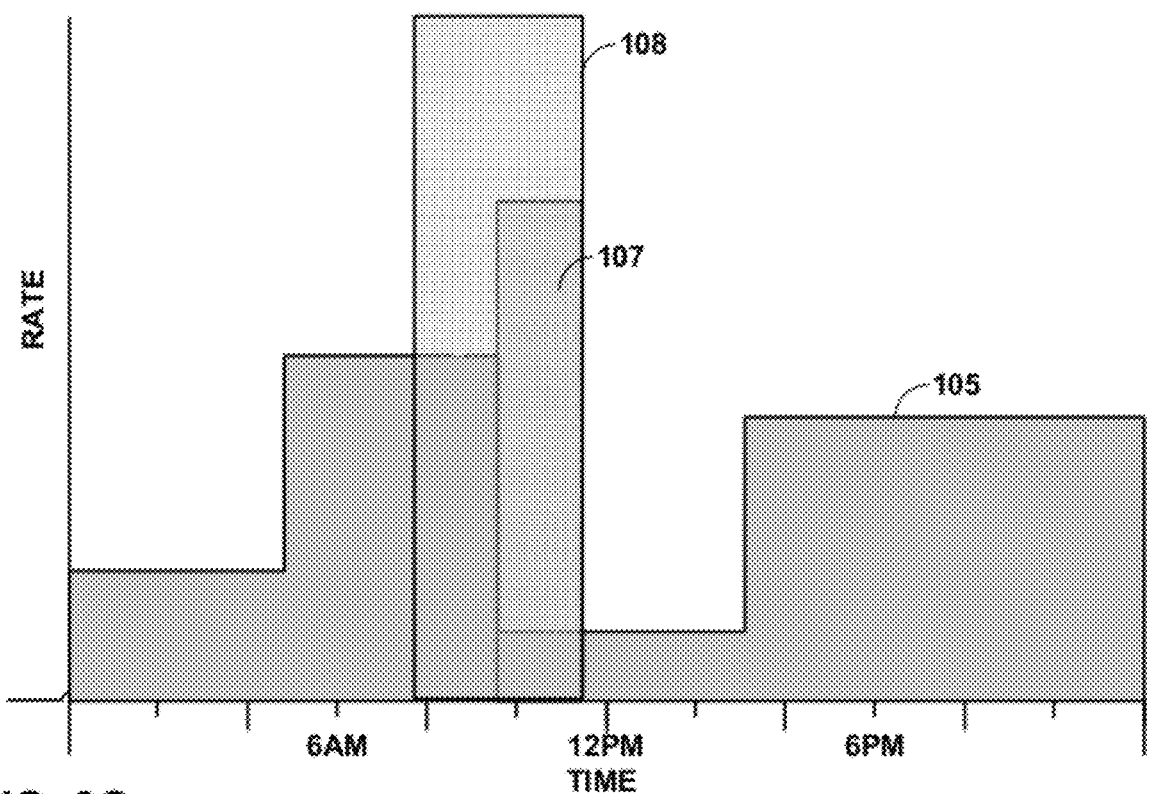

In FIG. 6B, box 107 overlaps the portion the proposed therapy program corresponding to the "worst" case for the timing of the bolus during the proposed therapy program in term of overdose. In FIG. 6C, the duration of analysis window 108 is just longer than the duration of the authorized bolus 107. Analysis window 108 is shown overlapping this "worst" case such that the total dosage during the analysis window corresponds to the maximum dosage that patient 12 may be delivered by IMD 12 (in the case where a single bolus is authorized during a 24-hour period). Using the techniques described in this disclosure, processor 84 may compare to the total dosage proposed for delivery during analysis window 108 to a reference dosage, e.g., to determine whether to apply the proposed therapy dosing program based on this "worst" case.

Figure 6D:
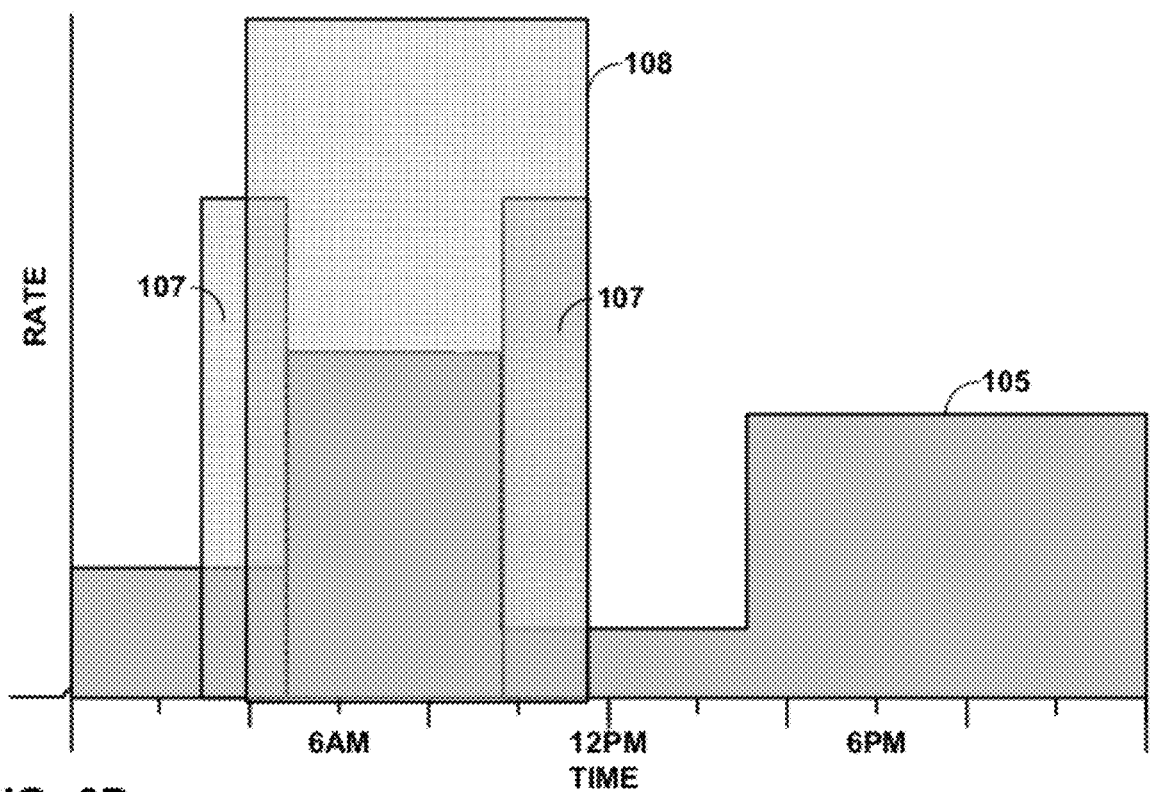

FIG. 6D represents the "worst" case for the timing of first and second boluses 107 during the proposed therapy program in term of overdose, e.g., when the proposed therapy program authorizes two boluses during a 24-hour period. In FIG. 6D, the duration of analysis window 108 is just longer than that shown in FIG. 6C. Analysis window 108 is shown overlapping this "worst" case such that the total dosage during the analysis window corresponds to the maximum dosage that patient 12 may be delivered by IMD 12. Again, processor 84 may compare to the total dosage proposed for delivery during analysis window 108 to a reference dosage, e.g., to determine whether to apply the proposed therapy dosing program based on this "worst" case.

Figure 6E:
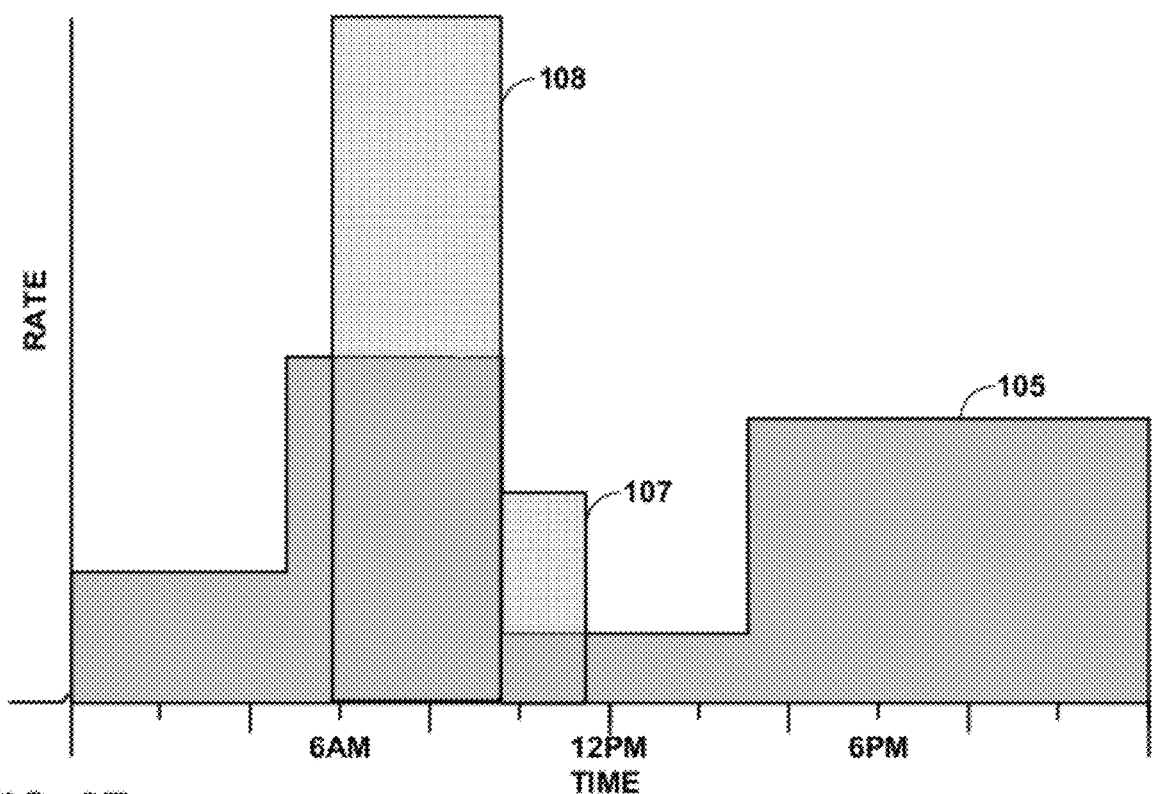

In FIG. 6E, box 107 overlaps the portion the proposed therapy program corresponding to the "worst" case for the timing of the bolus (in the case where a single bolus is authorized during a 24-hour period) during the proposed therapy program in term of overdose. Unlike that above, box 107 represents a bolus that has rate less than the maximum rate defined by the therapy schedule. As such, analysis window 108 does not overlap a portion of bolus 107 but instead overlaps a portion of the step defining the maximum rate. Again, processor 84 may compare to the total dosage proposed for delivery during analysis window 108 to a reference dosage, e.g., to determine whether to apply the proposed therapy dosing program based on this "worst" case.

Figure 6F:
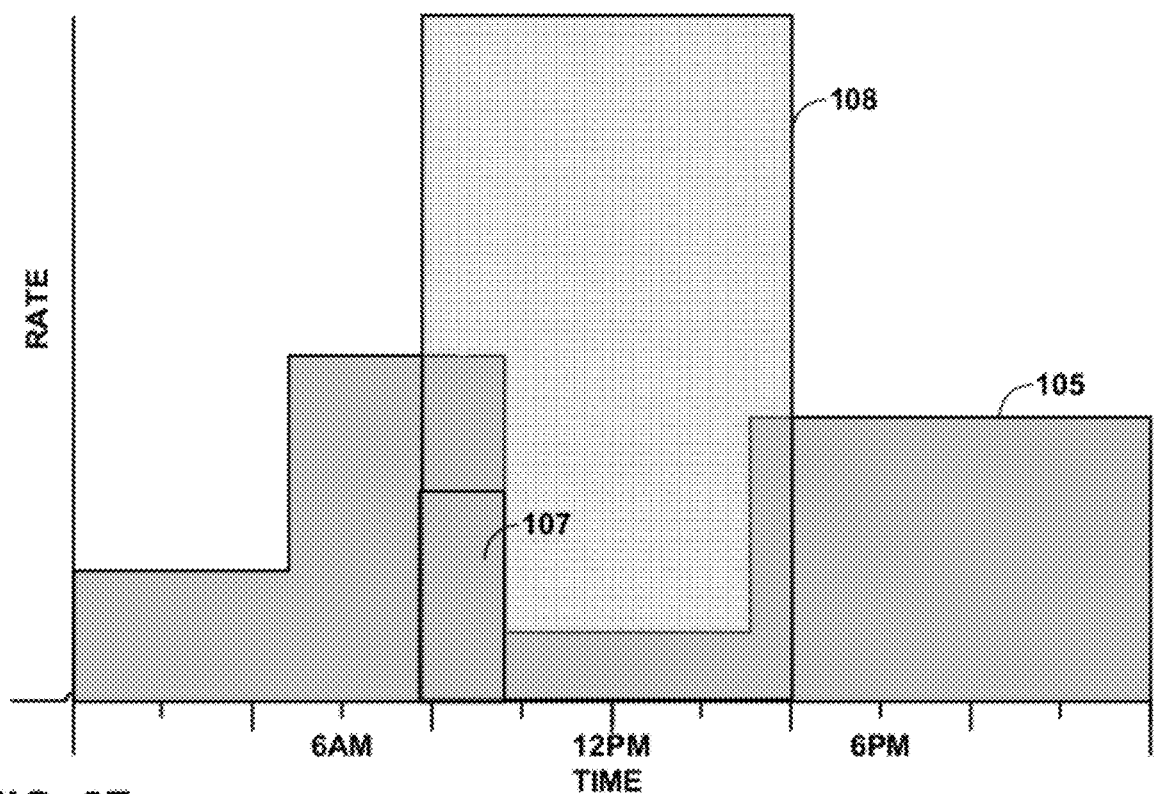

FIG. 6F illustrates an example similar to that of FIG. 6E. However, the duration of analysis window 108 is longer and the "worst" case is shown in terms of underdose rather than overdose. In the example of FIG. 6F, the bolus is delivered at a time that overrides a period of the therapy schedule defining the maximum rate. In such a case, such an override due to the bolus effectively lowers rate compared to that defined by a therapy schedule, and defines the "worst" case for the proposed therapy program in terms of underdose. As described above, processor 84 may compare to the total dosage proposed for delivery during analysis window 108 to a reference dosage range (and, in particular, the minimum references dosage value defined by the reference range), e.g., to determine whether to apply the proposed therapy dosing program based on this "worst" case.

In some examples, processor 84 may utilize one or more of the techniques described in this disclosure to evaluate multiple therapy dosing programs, either individually or in combination with one another. As described above, in some examples, the same therapy dosing program may be repeated to define therapy over a period of time that greater than the overall time period of the therapy dosing program. For example, a daily therapy dosing program may be repeated seven times to define therapy delivered to a patient over a week's time. Additionally or alternatively, in some examples, two or more different therapy dosing may be used in direct succession to define therapy delivered to patient 16 via IMD 12. In each case, there may be a period of time including a portion at the end of a first therapy dosing program and a portion at the beginning of the following therapy dosing program during which a potentially unacceptable dose may be programmed for delivery to patient 16 via IMD 12.

In accordance with one or more examples of the disclosure, processor 84 (and/or other processor) may evaluate two proposed dosing programs in combination with one another via an analysis window with one portion within one of the proposed therapy dosing programs and another portion within the other of the proposed therapy dosing programs. Similar to that described above, processor 84 may determine the total dosage proposed for delivery during such an analysis window, and compare the total dosage to a reference dosage defined based on the duration of analysis window. In some examples, processor 84 may determine whether to apply the combination of the two proposed therapy dosing programs based on the comparison.

Figure 7:
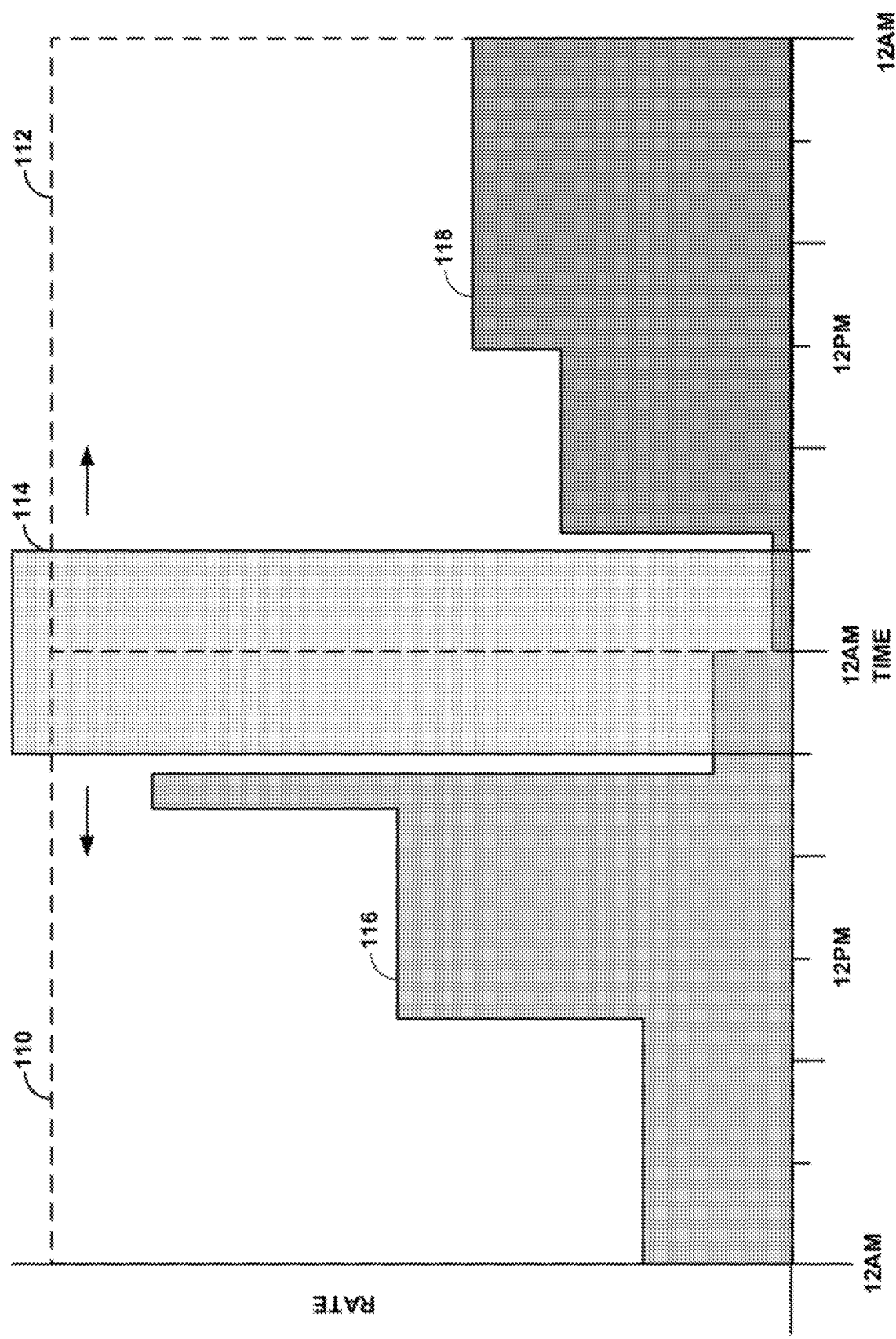
FIG. 7 is a conceptual diagram illustrating an example representation of an example therapy defined by two example therapy dosing programs.

FIG. 7 is a conceptual diagram illustrating example representation of an example therapy defined by two example therapy dosing programs. In particular, the example therapy of FIG. 7 is defined first by a first proposed therapy dosing program 110 followed by second proposed therapy dosing program 112. As shown, the overall time period of each proposed dosing program represented in FIG. 7 is approximately twenty-four hours. When used in combination with each other, first and second proposed therapy dosing programs 110, 112 may define therapy for delivery to patient 16 via IMD 12 over a period of approximately forty-eight hours.

In FIG. 7, line 116 represents the rate and duration defined by first proposed therapy dosing program 110, and line 118 represents the rate and duration defined by second proposed therapy dosing program 112. As described above, the rate and duration information for each proposed dosing program may be defined by therapy schedules and/or the potential for bolus delivery during the time periods of the respective dosing programs 110, 112. Although first and second therapy dosing programs 110, 112 are shown as being different with respect to rate and duration, in other examples, first and second therapy dosing programs 110, 112 may be substantially the same therapy dosing program.

A clinician may propose the combination of first therapy dosing program 110 followed by second therapy dosing program 112, e.g., using programmer 20 during a programming session, to define therapy over a forty-eight hour time period. Upon receipt of the proposed combination of first therapy dosing program 110 and second therapy dosing program 112, processor 84 may evaluate the proposed combination by determining the total dosage proposed for delivery within analysis window 114 during one or more periods overlapping the first therapy dosing program 110 and/or second therapy dosing program 112. In the example of FIG. 7, analysis window 114 has a duration of approximately 8 hours, although other durations are contemplated for analysis window 114.

As shown in FIG. 7, analysis window 114 may overlap a portion of first therapy dosing program 110 and a portion of second therapy dosing program 112, in which case the total dosage proposed for delivery during analysis window 114 determined by processor 84 depends on both first therapy dosing program 110 and second therapy dosing program 112. Additionally or alternatively, processor 84 may determine the total dosage for one or more analysis windows entirely within first therapy dosing program 110 and/or second therapy dosing program. Similar to that described above, analysis window 114 may be moved to a plurality of different locations (or "swept") over substantially all or portions of the overall time period defined by the combination of first therapy dosing program 110 and second therapy dosing program 112 to detect any periods of time during which the total dosage delivered to patient 16 would be outside the reference dosage range defined for the duration of analysis window 114.

As analysis window 114 may overlap portions of first therapy dosing program 110 and second therapy dosing program 112, by comparing the total dosage within analysis window 114 to a reference dosage range, processor 84 may identify time periods during which a potentially unacceptable dose may be programmed for delivery to patient resulting from the proposed combination of first therapy dosing program 112 and second therapy dosing program 114. This may be the case even if there are no time periods during first therapy dosing program 110 and second therapy dosing program 112, when evaluated individually, for which the total dosage within analysis window 114 is outside that of the reference dosage range.

In some examples, if processor 84 determines that the total dosage proposed for delivery when analysis window 114 overlaps a portion of both first therapy dosing program 110 and second therapy dosing program 114 is outside the reference dosage range, processor 84 may not directly apply the proposed combination to prevent IMD 12 from delivery therapy to patient 16 according to the proposed combination. Conversely, if processor 84 determines that there are no time periods for which the total dosage proposed for delivery when analysis window 114 overlaps a portion of one or both of first therapy dosing program 110 and second therapy dosing program 114 is outside the reference dosage range, processor 84 may apply first therapy dosing program 110 and second therapy dosing program 112, in the proposed combination, such that IMD 12 may deliver therapy to patient 16 according to the combination. Additionally or alternatively, processor 84 may present an indication of the comparison to a user via user interface 82, and user may indicate to programmer 84 via user interface 82 if the proposed therapy programs should be applied in combination to define therapy delivered to patient 12.

Figure 8:
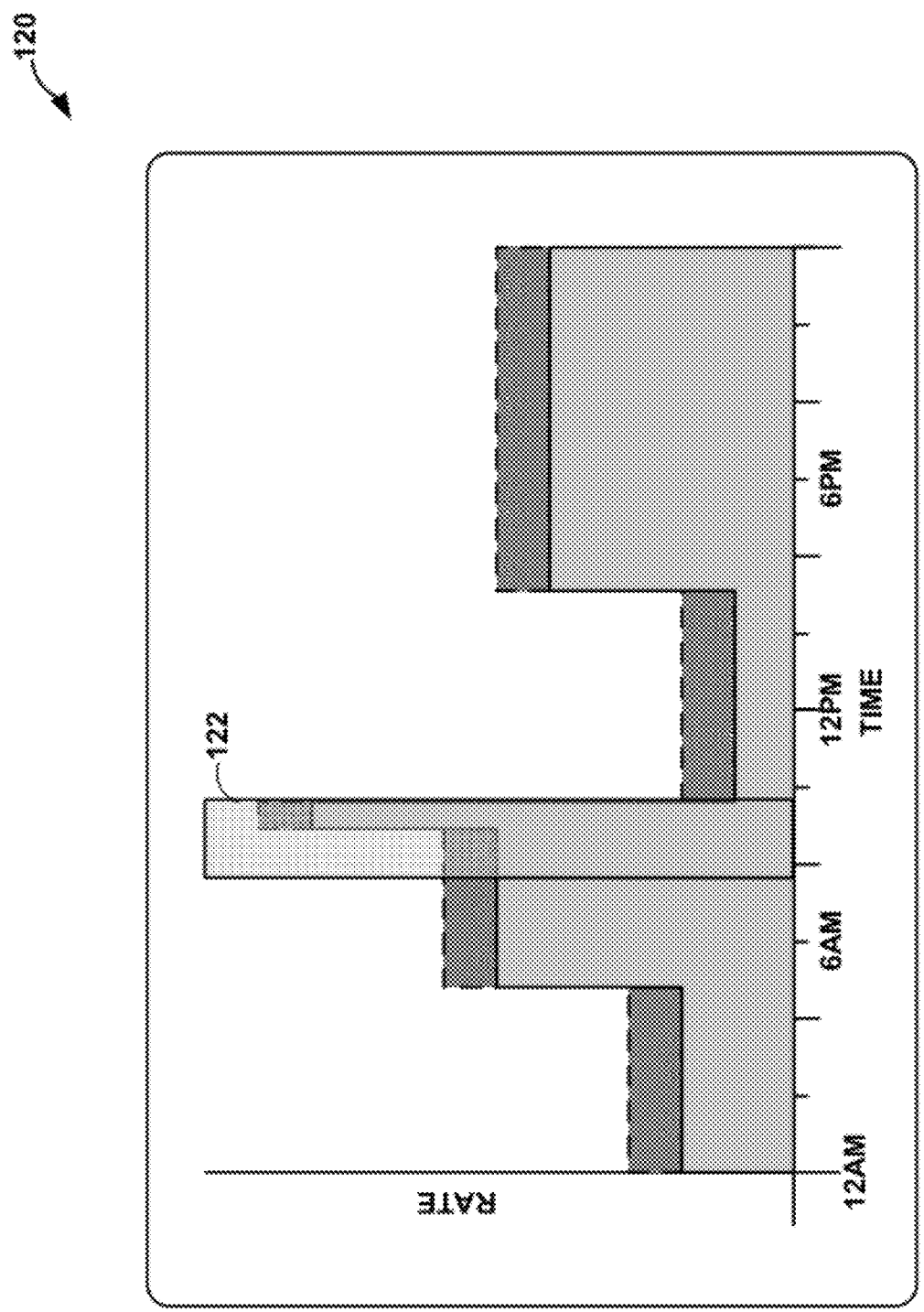
FIG. 8 is a conceptual diagram illustrating an example representation of a proposed therapy dosing program that may be displayed to a user via an example user interface.

FIG. 8 is a conceptual diagram illustrating an example screen 120 of example user interface 82 (FIG. 3) for displaying an indicator of one or more proposed therapy dosing program. Processor 84 may generate and display screen 120 via user interface 82 to allow a user to visualize one or more aspects of a proposed therapy dosing program. For example, as shown, screen 120 may display a plot of rate versus time over a period of twenty-four hours, as defined by a proposed therapy dosing program. For ease of illustration, in FIG. 8, screen 120 is shown displaying substantially the same proposed therapy dosing program shown in FIG. 5. However, any other proposed therapy dosing program or proposed combination of therapy dosing programs may be displayed in a substantially similar manner.

In some examples, screen 120 may be displayed by programmer 20 after processor 84 has determined that a proposed therapy dosing program defines a total dosage within one or more analysis windows outside a reference dosage range based on a comparison of the total dosage proposed for delivery during one or more analysis windows, as described above. In addition to displaying one or more therapy parameters (e.g., proposed rate and time) for a proposed therapy dosing program, screen 120 may also include an indicator indicating the one or more time periods for which the total dosage resulted in the rejection of the proposed therapy dosing program. For example, screen 200 includes highlighted indicator 122 which overlay a portion of the plot defined by the proposed therapy dosing program. As positioned, indicator 122 may correspond to an analysis window for which processor 84 has determined that the total dosage during the window is outside the reference dosage range. In this manner, indicator 122 may indicate to a clinician or other user the particular period of time during the proposed therapy dosing schedule that the total dosage may be unacceptable, as defined by the reference dosage range. Although screen 120 display only a single highlighted indicator 122 in FIG. 8, screen 120 may simultaneously or sequentially display a plurality of highlighted indicators at different period of time within the proposed therapy dosing program to indicate a plurality of analysis windows for which processor 84 has determined that the total dosage during the window is outside the reference dosage range.

Based in part on screen 120, a clinician or other user may determine what action to take after processor 84 has alerted the user to the results of the comparison. As noted above, in some examples, a clinician may input one or more modifications to the proposed therapy dosing program, particularly in relation to the therapy proposed for delivery during an analysis window for which the total dosage was outside the reference dosage range. Screen 120 may assist a clinician by identifying such time periods via highlighted indicator 122.

In some examples, a clinician may modify the rate or other therapy parameter (e.g., bolus authorization information) defined by proposed therapy dosing program during the period of time overlaid by highlighted indicator 122 using user interface 82 of programmer 20. Once modified, processor 84 may re-evaluate the proposed therapy dosing program, in the modified form, using one or more of the techniques described in this disclosure. In some examples, highlighted indicator 122 may remain on screen until the modification made to the proposed therapy dosing program results in a total dosage over the indicated time period that is within the reference dosage range.

In some examples, where processor 84 identifies multiple analysis windows defining a total dosage outside the reference dosage, screen 120 may sequentially move a clinician through such windows starting with the analysis window with the greatest difference between the total dosage and reference dosage and ending with the analysis window with the smallest difference between the total dosage and reference dosage. In some examples, a user may navigate through the multiple analysis windows using one or more buttons or other user feature of user interface 82. In some examples, screen 120 may present period of overdose and underdose to a user separately from one another.

In some examples, screen may also indicate the total dosage to a user within an analysis window and/or percent difference between the proposed total dosage and the average or reference dosage (e.g., via text or other graphical indicator). In some examples, screen 120 may indicate a recommended resolution or adjustment to the proposed therapy program to a user (e.g., including a breakout of contributors between repeating profiles, patient and/or clinician bolus).

In some examples, screen 120 and user interface 82 may allow a user to dismiss a specific alert for a specific analysis window or all alerts of a particular class, e.g., for a programming session or for a certain patient, drug, programmer, and the like. In some examples, a user may be able to exclude certain types of infusion (e.g., clinician or patient directed events) on a specific or global basis. In some examples, a user may be able to define or alter a reference dosage range or alter the duration of an analysis window, e.g., to increase or decrease the sensitivity of the evaluation.

All or some of the functionality and information described above may be presented immediately on screen 120 or hidden under an access method, such as, a button or context menu.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Various examples have been described. These and other examples are within the scope of the following claims.

The invention claimed is:

1. A method comprising:
    receiving, using one or more processors, a proposed therapy dosing program that defines delivery of a therapeutic agent over a first period of time to a patient via a medical fluid delivery device, the proposed therapy dosing program defining a nonzero rate for the delivery of the therapeutic agent to the patient via the medical fluid delivery device at a beginning of the first period of time;
    determining, using the one or more processors, a total dosage of the therapeutic agent over an analysis window based on the proposed therapy dosing program, wherein the total dosage is determined prior to applying the proposed therapy dosing program to control the delivery of the therapeutic agent to the patient, and wherein the analysis window begins after the beginning of the first period of time and only partially overlaps the first period of time, and the first period of time only partially overlaps the analysis window;
    comparing, using the one or more processors and prior to applying the proposed therapy dosing program to control the delivery of the therapeutic agent to the patient, the total dosage over the analysis window to a reference dosage defined based on a total duration of the analysis window;
    based on the comparison and using the one or more processors, selecting whether to control the delivery of the therapeutic agent to the patient via the medical fluid delivery device according to the proposed therapy dosing program or reject the proposed therapy dosing program; and
    based on the selection and using the one or more processors, controlling the delivery of the therapeutic agent to the patient via the medical fluid delivery device according to the proposed therapy dosing program or rejecting the proposed therapy dosing program.

2. The method of claim 1, wherein controlling the delivery of the therapeutic agent to the patient via the medical fluid delivery device according to the proposed therapy dosing program or rejecting the proposed therapy dosing program based on the selection comprises controlling, based on the selection, the delivery of the therapeutic agent to the patient via the medical fluid delivery device according to the proposed therapy dosing program.

3. The method of claim 1, further comprising presenting an indicator indicative of the comparison via a user interface.

4. The method of claim 1, wherein the reference dosage comprises a reference dosage range, and wherein comparing the total dosage over the analysis window to the reference dosage comprise determining whether the total dosage is within the reference dosage range.

5. The method of claim 4, further comprising presenting an indicator indicative of the comparison via a user interface, wherein the indicator indicative of the comparison presented via the user interface comprises an indicator indicative of whether the total dosage is within the reference dosage range.

6. The method of claim 1, wherein controlling the delivery of the therapeutic agent to the patient via the medical fluid delivery device according to the proposed therapy dosing program or rejecting the proposed therapy dosing program based on the selection comprises rejecting the proposed therapy dosing program based on the selection.

7. The method of claim 6, further comprising:
receiving, following the rejection, a modification to the proposed therapy dosing program;
determining, using the modified proposed therapy dosing program, a total dosage over the analysis window; and
comparing the total dosage over the analysis window determined for the modified proposed therapy dosing program to the reference dosage.

8. The method of claim 1, wherein the total duration of the analysis window is less than a total duration of the first period of time.

9. The method of claim 1, wherein the analysis window comprises a first analysis window, the method further comprising:
determining a total dosage over a second analysis window, wherein the second analysis window at least partially overlaps the first period of time; and
comparing the total dosage over the second analysis window to a reference dosage defined based on a total duration of the second analysis window.

10. The method of claim 9, wherein the total duration of the second analysis window is different than the total duration of the first analysis window.

11. The method of claim 1, wherein the proposed therapy dosing program includes a therapy schedule defining rate and duration for delivery of the therapeutic agent during the first period of time.

12. A system comprising:
a medical fluid delivery device configured to deliver a therapeutic agent to a patient; and
a processor configured to receive a proposed therapy dosing program that defines delivery of a therapeutic agent over a first period of time to the patient via the medical fluid delivery device, the proposed therapy dosing program defining a nonzero rate for the delivery of the therapeutic agent to the patient via the medical fluid delivery device at a beginning of the first period of time, determine a total dosage over an analysis window based on the proposed therapy dosing program, wherein the total dosage is determined prior to applying the proposed therapy dosing program to control the delivery of the therapeutic agent to the patient, and wherein the analysis window begins after the beginning of the first period of time and only partially overlaps the first period of time, and the first period of time only partially overlaps the analysis window, compare, prior to applying the proposed therapy dosing program to control the delivery of the therapeutic agent to the patient, the total dosage over the analysis window to a reference dosage defined based on a total duration of the second period of time, and based on the comparison, selectively control the delivery of the therapeutic agent to the patient via the medical fluid delivery device according to the proposed therapy dosing program or reject the proposed therapy dosing program.

13. The system of claim 12, wherein the processor is configured to control, based on the comparison, the delivery of the therapeutic agent to the patient via the medical fluid delivery device according to the proposed therapy dosing program.

14. The system of claim 12, further comprising a user interface, wherein the processor is configured to present an indicator indicative of the comparison via the user interface.

15. The system of claim 12, wherein the reference dosage comprises a reference dosage range, and wherein the processor compares the total dosage over the analysis window to the reference dosage by at least determining whether the total dosage is within the reference dosage range.

16. The system of claim 15, further comprising a user interface, wherein the at least one processor is configured to present an indicator indicative of the comparison via the user interface, wherein the indicator indicative of the comparison presented via the user interface comprises an indicator indicative of whether the total dosage is within the reference dosage range.

17. The system of claim 12, wherein the processor is configured to reject the proposed therapy dosing program based on the comparison.

18. The system of claim 12, wherein the processor is configured to:
receive, following the rejection, a modification to the proposed therapy dosing program;
determine, using the modified proposed therapy dosing program, a total dosage over the analysis window; and
compare the total dosage over the analysis window determined for the modified proposed therapy dosing program to the reference dosage.

19. The system of claim 12, wherein the total duration of the analysis window is less than a total duration of the first period of time.

20. The system of claim 12, wherein the analysis window comprises a first analysis window, and wherein the processor is configured to:
determine a total dosage over a second analysis window, wherein the second analysis window at least partially overlaps the first period of time; and
compare the total dosage over the second analysis window to a reference dosage defined based on a total duration of the second analysis window.

21. The system of claim 20, wherein the total duration of the second analysis window is different than the total duration of the first analysis window.

22. The system of claim 12, wherein the proposed therapy dosing program includes a therapy schedule defining rate and duration for delivery of the therapeutic agent during the first period of time.

23. A system comprising:
means for receiving a proposed therapy dosing program that defines delivery of a therapeutic agent over a first period of time to a patient via a medical fluid delivery device, the proposed therapy dosing program defining a nonzero rate for the delivery of the therapeutic agent to the patient via the medical fluid delivery device at a beginning of the first period of time;
means for determining a total dosage of the therapeutic agent over an analysis window based on the proposed therapy dosing program, wherein the total dosage is determined prior to applying the proposed therapy dosing program to control the delivery of the therapeutic agent to the patient, and wherein the analysis window begins after the beginning of the first period of time and only partially overlaps the first period of time, and the first period of time only partially overlaps the analysis window;

means for comparing, prior to applying the proposed therapy dosing program to control the delivery of the therapeutic agent to the patient, the total dosage over the analysis window to a reference dosage defined based on a total duration of the analysis window; and means for, based on the comparison, selectively controlling the delivery of the therapeutic agent to the patient via the medical fluid delivery device according to the proposed therapy dosing program or rejecting the proposed therapy dosing program.

24. A non-transitory computer-readable storage medium comprising instructions that cause one or more processors to:

receive a proposed therapy dosing program that defines delivery of a therapeutic agent over a first period of time to a patient via a medical fluid delivery device, the proposed therapy dosing program defining a nonzero rate for the delivery of the therapeutic agent to the patient via the medical fluid delivery device at a beginning of the first period;

determine a total dosage of the therapeutic agent over an analysis window based on the proposed therapy dosing program, wherein the total dosage is determined prior to applying the proposed therapy dosing program to control the delivery of the therapeutic agent to the patient, and wherein the analysis window begins after the beginning of the first period of time and only partially overlaps the first period of time, and the first period of time only partially overlaps the analysis window;

compare, prior to applying the proposed therapy dosing program to control the delivery of the therapeutic agent to the patient, the total dosage over the analysis window to a reference dosage defined based on a total duration of the analysis window; and based on the comparison and using the one or more processors, selectively control the delivery of the therapeutic agent to the patient via the medical fluid delivery device according to the proposed therapy dosing program or reject the proposed therapy dosing program.

25. The system of claim 12, wherein the total duration of the analysis window is approximately equal to a total duration of the first period of time.

26. The system of claim 12, wherein the reference dosage comprises a first reference dosage, wherein the total dosage comprises a first total dosage, and wherein the processor is configured to determine a second total dosage over the first period of time based on the proposed therapy dosing program, and compare the second total dosage over the first period of time to a second reference dosage defined based on a total duration of the first period of time.

27. The method of claim 1, wherein the proposed therapy dosing program comprises a first proposed therapy dosing program that defines delivery of the therapeutic agent over the first period of time to the patient via the medical fluid delivery device, the method further comprising receiving a second proposed therapy dosing program that defines delivery of the therapeutic agent over a second period of time to the patient via the medical fluid delivery device, wherein the second period of time follows the first period of time and does not overlap the first period of time, and wherein the analysis window overlaps a portion of the second period of time.

28. The method of claim 27, wherein the analysis window only partially overlaps the second period of time and the second period of time only partially overlaps the analysis window.

29. The method of claim 27, wherein the first proposed therapy dosing program and the second proposed therapy dosing program define substantially a same delivery of the therapeutic agent to the patient.

30. The system of claim 12, wherein the proposed therapy dosing program comprises a first proposed therapy dosing program that defines delivery of the therapeutic agent over the first period of time to the patient via the medical fluid delivery device, wherein the processor is configured to receive a second proposed therapy dosing program that defines delivery of the therapeutic agent over a second period of time to the patient via the medical fluid delivery device, wherein the second period of time follows the first period of time and does not overlap the first period of time, and wherein the analysis window overlaps a portion of the second period of time.

31. The system of claim 30, wherein the analysis window only partially overlaps the second period of time and the second period of time only partially overlaps the analysis window.

32. The system of claim 30, wherein the first proposed therapy dosing program and the second proposed therapy dosing program define substantially a same delivery of the therapeutic agent to the patient.

33. The method of claim 11, wherein a rate of the delivery of the therapeutic agent varies during the first period of time according to the proposed therapy dosing program.

34. The method of claim 2, wherein controlling the delivery of the therapeutic agent to the patient via the medical fluid delivery device according to the proposed therapy dosing program comprises delivering the therapeutic agent to the patient from the medical fluid delivery device continuously throughout the first period according to the proposed therapy dosing program.

35. The system of claim 22, wherein a rate of the delivery of the therapeutic agent varies during the first period of time according to the proposed therapy dosing program.

36. The system of claim 12, wherein the processor is configured to control delivery of the therapeutic agent to the patient via the medical fluid delivery device such that the therapeutic agent is continuously delivered throughout the first period according to the proposed therapy dosing program.

* * * * *